(12) United States Patent
Zhang et al.

(10) Patent No.: US 8,334,255 B2
(45) Date of Patent: Dec. 18, 2012

(54) PEPTIDE AND TREATMENT FOR HIV-1 INFECTION

(75) Inventors: Hui Zhang, Voorhees, NJ (US); Harold C. Smith, Rochester, NY (US)

(73) Assignees: Thomas Jefferson University, Philadelphia, PA (US); OyaGen Inc., Rochester, NY (US)

(*) Notice: Subject to any disclaimer, the term of this patent is extended or adjusted under 35 U.S.C. 154(b) by 490 days.

(21) Appl. No.: 12/448,058

(22) PCT Filed: Dec. 4, 2007

(86) PCT No.: PCT/US2007/024790
§ 371 (c)(1),
(2), (4) Date: Jun. 5, 2009

(87) PCT Pub. No.: WO2008/070049
PCT Pub. Date: Jun. 12, 2008

(65) Prior Publication Data
US 2010/0029570 A1    Feb. 4, 2010

Related U.S. Application Data

(60) Provisional application No. 60/873,186, filed on Dec. 6, 2006.

(51) Int. Cl.
*A61K 38/16* (2006.01)
*A61K 38/08* (2006.01)
*C07K 14/00* (2006.01)
*C07K 7/06* (2006.01)
*C07K 7/08* (2006.01)

(52) U.S. Cl. ........... 514/3.8; 514/1.1; 514/3.7; 530/324; 530/325; 530/326; 530/327; 530/328

(58) Field of Classification Search .................. None
See application file for complete search history.

(56) References Cited

U.S. PATENT DOCUMENTS

| | | | | |
|---|---|---|---|---|
| 5,595,756 | A * | 1/1997 | Bally et al. | 424/450 |
| 6,653,443 | B2 | 11/2003 | Zhang et al. | 530/327 |
| 7,226,741 | B2 | 6/2007 | Zhang et al. | 435/6 |
| 7,498,138 | B2 | 3/2009 | Zhang et al. | 435/6 |
| 2004/0138133 | A1 | 7/2004 | Cheresh et al. | 514/13 |
| 2005/0287648 | A1 | 12/2005 | Smith et al. | 435/91.1 |

FOREIGN PATENT DOCUMENTS

| | | |
|---|---|---|
| EP | 0 330 359 | 2/1989 |
| WO | WO 02/081504 | 10/2002 |

OTHER PUBLICATIONS

Definition of derivative and analog from http://cancerweb.ncl.ac.uk/omd/about.html, pp. 1-5. Accessed Jul. 7, 2005.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Hendrix CW, Flexner C, MacFarland RT, Giandomenico C, Fuchs EJ, Redpath E, Gridger G, Henson GW, "Pharmacokinetics and Safety of AMD-3100, a Novel Antagonist of the CXCR-4 Chemomkine Receptor, in Human Volunteers," ANtimicrobial Agents and Chemotherapy, 2000, 44(6): 1667-1673.*
Buss N, Snell P, Bock J, Hsu A, Jorga K, "Saquinavir and ritonavir pharmacokinectis following combined ritonavir and saquinavir (soft gelatin capsules) administration," J. Cln. Pharmacol., 2001, 52: 255-264.*
Gait MJ, Karn J, "Progress in Anti-HIV structure-based drug design," TIBTECH, 1995, 430-438.*
Yin PD, Das D, Mitsuya H, "Overcoming HIV drug resistance through rational drug design based on molecular, biochemical, and structural profiles of HIV resistance," Cell. Mol. Life Scie, 2006, 63: 1706-1724.*
Sporn MB, Suh N, "Chemoprevention of cancer," Carcinogenesis, 2000, 21(3): 525-530.*
Gura T, "Cancer Models: Systems for Identifying New Drugs Are Often Faulty," Science, 1997, 278: 1041-1042.*
Yang, et al., "Potent Suppression of Viral Infectivity by the Peptides That Inhibit Multimerization of Human Immunodeficiency Virus Type 1 (HIV-1) Vif Proteins", *The Journal of Biological Chemistry*, vol. 278, No. 8, pp. 6596-6602 (2003).
Yang, et al., "The Multimerization of Human Immunodeficiency Virus Type I Vif Protein", *The Journal of Biological Chemistry*, vol. 276, No. 7, pp. 4889-4893 (2001).
Friedler, et al., "Peptides Derived from HIV-1 Vif: A Non-substrate Based Novel Type of HIV-1 Protease Inhibitors", *J. Mol. Biol.* (1999) 287, 93-101.

* cited by examiner

*Primary Examiner* — Julie Ha
(74) *Attorney, Agent, or Firm* — Drinker Biddle & Reath LLP

(57) ABSTRACT

A compound of the formula $X^1$-M-SEQ ID NO:1, or a derivative thereof, is provided, wherein $X^1$-M- represents an optional group comprising a protein transduction domain conjugated to the N-terminus of the amino acid sequence SEQ ID NO:1. Pharmaceutical compositions comprising and therapeutic methods using the compound are also provided.

22 Claims, 9 Drawing Sheets

PEPTIDE AND TREATMENT FOR HIV-1 INFECTION

FIELD OF THE INVENTION

The invention relates to compounds, compositions, and methods for the treatment of infection with human immunodeficiency virus type 1 (HIV-1) and acquired immune deficiency syndrome (AIDS).

BACKGROUND OF THE INVENTION

HIV-1, a human lentivirus, is the major causative agent of AIDS, which presently infects approximately 42 million persons worldwide with 1 million infected persons in North America.

Although considerable effort is being put into the design of effective therapeutics, currently available drugs are not effective to cure AIDS. In attempts to develop such drugs, several stages of the HIV-1 life cycle have been considered as targets for therapeutic intervention (H. Mitsuya, et al., *FASEB J.*, 1991, 5, 2369-81). Many viral targets for intervention with HIV-1 life cycle have been suggested. A schematic illustration of the life-cycle of HIV-1, showing some of the potential drug targets for the treatment of HIV-1 infection and AIDS is illustrated in FIG. 1. Most of the currently available treatments inhibit reverse transciptase enzyme or the HIV-1 protease enzyme. Recently, enfuvirtide, a drug with a new mechanism of action was approved. Enfuvirtide is a peptide that binds to a region of the envelope glycoprotein 41 of HIV-1 that is involved in the fusion of the virus with the membrane of the CD4 positive host cell, and thereby inhibits fusion of HIV-1 with the membrane of the CD4 positive cells (J. P. Lalezari, et al., "Enfurvirtide, an HIV-1 fusion inhibitor, for drug-resistant HIV infection in North and South America", *N. Engl. J. Med.*, 2003, 348, 2175-85).

The new treatment regimens for HIV-1 show that a combination of anti-HIV compounds, which target reverse transcriptase (RT), such as azidothymidine (AZT), lamivudine (3TC), dideoxyinosine (ddI), dideoxycytidine (ddC) used in combination with an HIV-1 protease inhibitor have a far greater effect (2 to 3 logs reduction) on viral load compared to AZT alone (about 1 log reduction). One such example is a combination of AZT, ddI, 3TC and ritonavir (A. S. Perelson, et al., *Science*, 1996, 15:1582-86).

Table 1 lists the drugs currently approved by the United States Food and Drug Administration for the treatment of HIV infection and AIDS.

TABLE 1

United-States Food and Drug Administration Approved Drugs Treatment of HIV-1 Infection and AIDS

| Drug Class | Drug |
|---|---|
| Nuceloside reverse transcriptase inhibitor | lamivudine and zidovudine |
| Nuceloside reverse transcriptase inhibitor | emtricitabine, FTC |
| Nuceloside reverse transcriptase inhibitor | lamivudine, 3TC |
| Nuceloside reverse transcriptase inhibitor | abacavir and lamivudine |
| Nuceloside reverse transcriptase inhibitor | zalcitabine, dideoxycytidine, ddC |
| Nuceloside reverse transcriptase inhibitor | zidovudine, azidothymidine, AZT, ZDV |
| Nuceloside reverse transcriptase inhibitor | abacavir, zidovudine, and lamivudine |
| Nuceloside reverse transcriptase inhibitor | tenofovir disoproxil fumarate and emtricitabine |
| Nuceloside reverse transcriptase inhibitor | enteric coated didanosine, ddI EC |
| Nuceloside reverse transcriptase inhibitor | didanosine, dideoxyinosine, ddI |
| Nuceloside reverse transcriptase inhibitor | tenofovir disoproxil fumarate, TDF |
| Nuceloside reverse transcriptase inhibitor | stavudine, d4T |
| Nuceloside reverse transcriptase inhibitor | abacavir sulfate, ABC |
| Non-nuceloside reverse transcriptase inhibitor | delavirdine, DLV |
| Non-nuceloside reverse transcriptase inhibitor | efavirenz, EFV |
| Non-nuceloside reverse transcriptase inhibitor | nevirapine, NVP |
| Protease inhibitor | amprenavir, APV |
| Protease inhibitor | tipranavir, TPV |
| Protease inhibitor | indinavir, IDV, |
| Protease inhibitor | saquinavir mesylate, SQV |
| Protease inhibitor | lopinavir and ritonavir, LPV/RTV |
| Protease inhibitor | Fosamprenavir Calcium, FOS-APV |
| Protease inhibitor | ritonavir, RTV |
| Protease inhibitor | darunavir |
| Protease inhibitor | atazanavir sulfate, ATV |
| Protease inhibitor | nelfinavir mesylate, NFV |
| Fusion inhibitor | Enfuviritide, T-20 |
| Multi-class combination | efavirenz, emtricitabine and tenofovir disoproxil fumarate |

In spite of these advances, the need remains for new drugs that are effective against HIV-1 infection and AIDS. It is possible that long-term use of combinations of these chemicals that comprise the currently available treatments will lead to toxicity, especially to the bone marrow. Long-term cytotoxic therapy may also lead to suppression of CD8 positive T cells, which are essential to the control of HIV, via killer cell activity (V. Blazevic, et al., *AIDS Res. Hum. Retroviruses*, 1995, 11, 1335-42) and by the release of suppressive factors, notably the chemokines Rantes, MIP-1α and MMIP-1β (F. Cocchi, et al., *Science*, 1995, 270, 1811-1815). Another major concern in long-term chemical anti-retroviral therapy is the development of HIV mutations with partial or complete resistance (J. M. Lange, *AIDS Res. Hum. Retroviruses*, 1995, 10, S77-82). Such mutations may be an inevitable consequence of anti-viral therapy. The pattern of disappearance of wild-type virus and appearance of mutant virus due to treatment, combined with coincidental decline in CD4 positive T cell numbers strongly suggests that, at least with some compounds, the appearance of viral mutants is a major underlying factor in the failure of AIDS therapy.

The HIV-1 virus contains a 10-kb single-stranded, positive-sense RNA genome that encodes three major classes of gene products that include: (i) structural proteins such as Gag, Pol and Env; (ii) essential trans-acting proteins (Tat, Rev); and (ii) "auxiliary" proteins that are not required for efficient virus replication in at least some cell culture systems (Vpr, Vif, Vpu, Nef).

One approach to treating individuals infected with HIV-1 is to administer to such individuals compounds that directly intervene in and interfere with the machinery by which HIV-1 replicates itself within human cells.

One such protein, Vif (viral infectivity factor), is expressed by all known lentiviruses except equine infectious anemia virus. Vif protein of HIV-1 is a highly basic, 23-kDa protein composed of 192 amino acids. Sequence analysis of viral DNA from HIV-1-infected-individuals has revealed that the open reading frame of Vif remains intact. (P. Sova, et al., *J. Virol.* 1995, 69, 2557-64; U. Wieland, et al., *Virology,* 1994, 203, 43-51; U. Wieland, et al., *J. Gen. Virol.,* 1997, 78, 393-400). Vif is required for efficient virus replication in vivo, as well as in certain host cell types in vitro because of its ability to overcome the action of a cellular antiviral system. Deletion of the Vif gene dramatically decreases the replication of simian immunodeficiency virus (SIV) in macaques and HIV-1 replication in SCID-hu mice (G. M. Aldrovandi, et al., *J. Virol.,* 1996, 70, 1505-11; R. C. Desrosiers, et al., *J. Virol.,* 1998, 72, 1431-37), indicating that the Vif gene is essential for the pathogenic replication of lentiviruses in vivo.

Recent studies have elucidated the mechanism underlying the importance of Vif to the replication of HIV-1 viruses in vivo, which is associated with the anti-viral effect of a host protein called hA3G (APOBEC3G) (CEM15). hA3G belongs to a family of cytidine deaminases which induces G to A hypermutation in newly synthesized viral cDNA. Packaging of hA3G into virus particles can result in hypermutation of the viral minus-strand cDNA during reverse transcription, thereby interfering with the replication of the virus. R. S. Harris, et al., *Cell,* 2003, 113, 803-09; B. Mangeat, et al., *Nature,* 2003, 424, 99-103. Consistent with the antiviral effect of hA3G, correlations have been observed between hA3G mRNA levels and HIV viral load and CD4 cell count, both of which are predictors of HIV disease progression in patients who have not received antiretroviral drugs or other forms of therapeutic intervention. In addition, it was found that HIV-infected patients who show a low rate of disease progression even in the absence of antiviral treatment ("long term non-progressors") have significantly higher hA3G mRNA levels than do HIV-uninfected controls or the progressors, whose hA3G mRNA levels are significantly lower that of HIV-uninfected controls. X. Jin, et al., *J. Virol.,* 2005, 79(17), 11513-16.

The importance of Vif to HIV-1 replication is believed to be due to its role in overcoming the host defense mechanism provided by hA3G. Vif counteracts the antiviral activity of hA3G by targeting it for destruction by the ubiquitin-proteasome pathway. Vif forms a complex with hA3G and enhances hA3G ubiquitination, thereby targeting hA3G for degradation via the ubiquitin-proteasome pathway. A. Mehle, et al., *J. Biol. Chem.,* 2004, 279(9), 7792-98. B. R. Cullen, J. Virol. 2006, 80, 1067-76.

While the detailed molecular mechanism of the effect of Vif in evading host cell defense to HIV-1 remains to be elucidated, it has been hypothesized that Vif self-association to form multimers may play a key role, and the multimerization of Vif has been found to be required for Vif function in the viral life cycle. S. Yang, et al., *J. Biol. Chem.,* 2001, 276(7), 4889-93. It has been demonstrated that Vif aggregation is not simply due to fortuitous aggregation, but that a specific domain affecting Vif self-association is located at the C terminus of this protein, especially the proline-enriched 151-164 region, is implicated in Vif multimerization.

In cell culture systems, Vif-deficient (Vif⁻) HIV-1 is incapable of establishing infection in certain cells, such as H9 T cells, peripheral blood mononuclear cells, and monocyte-derived macrophages. This has led to classification of these cells as nonpermissive. In other cells, the Vif gene is not required; these cells have been classified as permissive. Using this phenomenon, Yang, et al., demonstrated that Vif aggregation (multimerization) is essential to the role of Vif in promoting viral infectivity. Yang, et al. tested various Vif mutants in a modified single-round viral infectivity assay. Wild-type Vif or its mutants were expressed in the nonpermissive H9 T-cells. At the same time, pseudotyped (with VSV envelope) HIV-1 viruses, without vif and env in their genome, were generated from these cells. The recombinant viruses were allowed to infect target cells harboring an expression cassette containing the HIV-1 long terminal repeat promoter-driven CAT gene. The viral infectivity was measured by the level of CAT gene expression in the target cells. When the wild-type Vif gene was expressed in the Vif-defective HIV-1 virus-producing nonpermissive H9 T-cells, a high level of viral infectivity was observed. However, when a Vif mutant lacking the binding region (VifΔ151-164) was expressed in the Vif-defective HIV-1 virus-producing nonpermissive H9 T-cells, the viral infectivity was almost unaltered, compared with the Vif-defective HIV-1 viruses, indicating that the deletion severely decreased the function of Vif protein and made it unable to rescue the infectivity of the Vif-defective HIV-1 viruses generated from nonpermissive T-cells. This experiment demonstrated that multimerization of Vif proteins is required for Vif function. S. Yang, et al., *J. Biol. Chem.,* 2001, 276(7), 4889-93. A scanning mutational analysis of Vif also demonstrated the importance of the binding region to infectivity, particularly the three residues (PPL) at 161-163. These could be substituted individually without loss of function, but substitution of all three residues severely inhibited function. J. H. M. Simon, et al., *J. Virol,* 1999, 73(4), 2675-81.

The discovery that multimerization of Vif proteins is required for Vif function in the viral life cycle, has led to it being proposed as a potential novel target for anti-HIV-1 therapeutics. The hypothesis is illustrated in FIGS. 2A and 2B. As shown by the above-mentioned studies, Vif multimerization is believed to be essential to Vif's action in an HIV-1 infected cell. When Vif functions normally in the cytoplasm, it is believed that Vif dimerizes and that the resulting Vif dimers target hA3G for modification through ubiquitination; and that as a consequence the hA3G is destroyed by the proteosome, and the HIV life cycle is not interrupted. Thus, when Vif functions normally, the virus overcomes the anti-infective function of hA3G. However, when Vif function is compromised (e.g. through the action of a drug that inhibits Vif dimerization, although HIV-1 would still be able to bind CD4 and enter T-cells, the hA3G would hypermutates the viral DNA during reverse transcription resulting in mutated viral DNAs that are either destroyed or integrated in defective form into the chromosomal DNA. If the mutated DNA is transcribed, the resulting RNA would encode few or no functional proteins and most of the HIV-1 viruses produced by the cell would be defective and non-infective.

Yang, et al. identified peptides containing a PXP motif that bind to HIV-1 Vif protein. These proline-enriched peptides were found to inhibit the Vif-Vif interaction in vitro. In addition, peptides covering all the amino acids of the HIV-1 Vif protein sequence were prepared and it was found that proline-enriched peptides that contain the $^{161}$PPLP$^{164}$ domain were able to inhibit the Vif-Vif interaction. The study concluded that the proline-enriched peptides block the multimerization of Vif through interfering with the polyproline interfaces of Vif formed by the $^{161}$PPLP$^{164}$ domain. Moreover, these peptides which inhibit the Vif-Vif interaction in vitro were found to inhibit HIV-1 replication in the "nonpermissive" T-cells. B. Yang, et al., *J. Biol. Chem.,* 2003, 278(8), 6596-602.

SUMMARY OF THE INVENTION

According to the invention, compounds and compositions are provided that inhibit Vif multimerization and which are effective against HIV-1 useful for treating diseases or conditions in which Vif multimerization is required for viral replication, including HIV-1 infection and AIDS.

As one aspect of the invention, there is provided a compound of the formula I:

$$X^1\text{-M-SEQ ID NO:1} \qquad (I)$$

or a derivative thereof, wherein:

$X^1$-M- represents an optional group comprising a protein transduction domain conjugated to the N-terminus of the amino acid sequence SEQ ID NO:1, wherein:

$X^1$ represents the protein transduction domain; and

-M- represents a single bond or an optional linking group forming a covalent linkage between the protein transduction domain and the amino acid sequence SEQ ID NO:1;

provided that if the compound comprises an amino acid directly bound to the N-terminus of the amino acid sequence SEQ ID NO:1, then the amino acid directly bound to the said N-terminus is other than asparagine.

Particular embodiments of the invention are those wherein the compound according to formula I is a peptide of the amino acid sequence SEQ ID NO: 1 or a peptide of the amino acid sequence SEQ ID NO:2.

Other particular embodiments of the invention are those wherein the compound according to formula I, comprises the amino acid sequence SEQ ID NO:3.

Other particular embodiments of the invention are those wherein the protein transduction domain comprises and optionally consists of an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34, preferably SEQ ID NO:4, SEQ ID NO:5, SEQ ID NO:6, SEQ ID NO:7, SEQ ID NO:8, SEQ ID NO:9, SEQ ID NO:10, or SEQ ID NO:11, most preferably SEQ ID NO: 4.

As another aspect of the invention, there is provided a pharmaceutical composition comprising a pharmaceutically acceptable carrier and a compound according to formula I.

As another aspect of the invention, there is provided a method of treating a disease or condition in which Vif protein multimerization is required for viral replication in an individual, comprising administering to an individual in need of such treatment a therapeutically effective amount of a compound according to the invention, or any of the embodiments thereof.

A method of treating or preventing HIV-1 infection is provided, comprising administering to an individual in need of such treatment a therapeutically effective amount of a compound according to the invention, or any of the embodiments thereof.

A method of treating or preventing acquired immune deficiency syndrome (AIDS) infection is provided, comprising administering to an individual in need of such treatment a therapeutically effective amount of a compound according to the invention, or any of the embodiments thereof.

BRIEF DESCRIPTION OF THE FIGURES

(FIG. 2A)): (1) Vif dimerizes in the cytoplasm (the dimerization is essential to Vif function); (2) the Vif dimers target hA3G for modification through ubiquitination; and (3) the hA3G is destroyed by the proteosome, and the HIV life cycle is not interrupted. When Vif function is compromised (e.g. through inhibition of dimerization) (FIG. 2B): (1) HIV-1 binds to T-cells; (2) as the HIV converts its RNA to DNA, hA3G hypermutates the viral DNA; (3) mutated viral DNAs are destroyed and those that integrate into chromosomal DNA are defective; (4) when copies of the mutated viral RNA are made, due to the hypermutation, the resulting RNA encodes few or no functional proteins; and (5) consequently, most of the HIV-1 viruses produced will be defective and non-infective.

DETAILED DESCRIPTION OF THE INVENTION

I. Definitions

Figure 1:
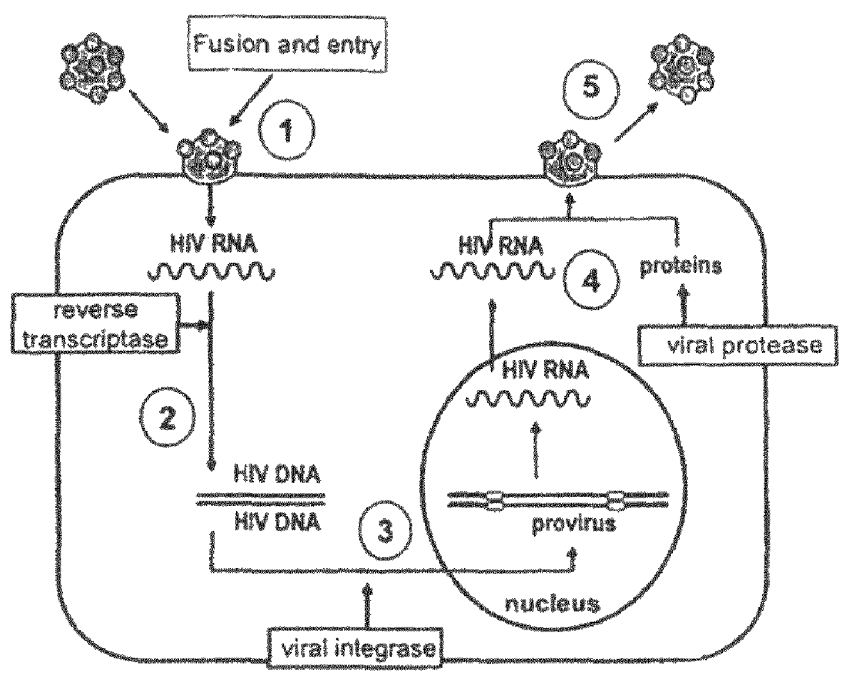
FIG. 1. Schematic showing the life cycle of HIV, showing drug targets for therapeutic intervention. (i) HIV fuses to immune system cells, releasing its RNA; (2) HIV RNA is converted to DNA by the action of reverse transcriptase; (3) the viral DNA enters the host cell nucleus and is integrated in the host cell chromosomal DNA by the action of HIV integrase; the viral RNA is made and the proteins produced and HIV protease processes proteins for viral assembly; and (5) HIV viruses bud from the cell and proceed to infect other cells.
Figure 2A:
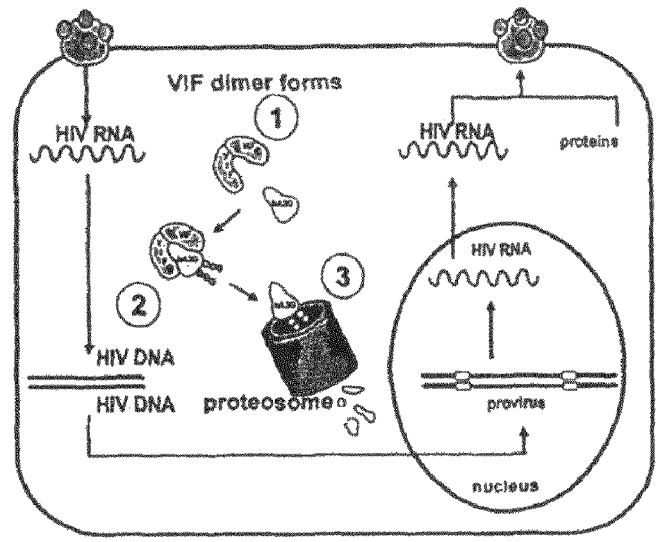
FIGS. 2A and 2B. Schematic diagrams showing the proposed mechanism of action of Vif antagonists. When Vif functions normally in the cytoplasm.
Figure 2B:
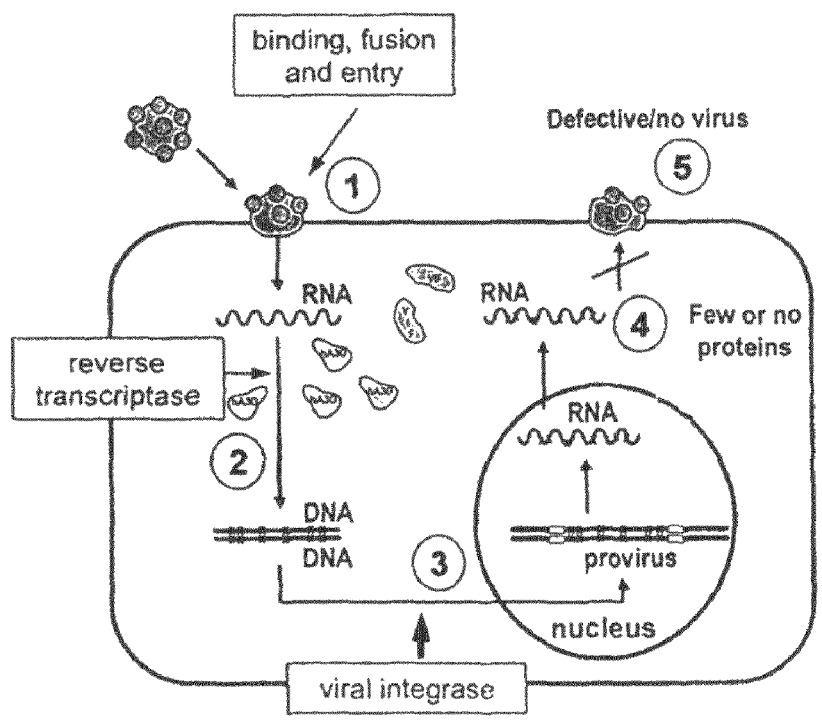

As used in the specification and the appended claims, the singular forms "a," "an" and "the" include plural referents unless the context clearly dictates otherwise.

The expressions "treat" and "treatment" mean cause, or the act of causing, a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

The expression "effective amount", when used to describe therapy to an individual, refers to the amount of a compound that results in a therapeutically useful effect.

As used herein, "individual" (as in the subject of the treatment) means mammals, particularly non-human primates, e.g. apes and monkeys, and most particularly humans.

Peptides are defined herein as organic compounds comprising a chain of two or more amino acids covalently joined by peptide bonds. Peptides may be referred to with respect to the number of constituent amino acids, i.e., a dipeptide contains two amino acid residues, a tripeptide contains three, etc. A "peptide" as used in the presently claimed invention is intended to refer to a moiety with a molecular weight of less than 10,000 Daltons, preferable less than 5,000 Daltons, and more preferably less than 2,500 Daltons.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but is usually do not occur in proteins. Included within this term are modified and unusual amino acids, such as those disclosed in, for example, Roberts and Vellaccio (1983) *The Peptides*, 5:342-429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, beta.-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanocarboxylic acid, 1-aminocyclopropanecarboxylic acid, and 2-benzyl-5-aminopentanoic acid.

The term "peptide bond" means a covalent amide linkage formed by loss of a molecule of water between the carboxyl group of one amino acid and the amino group of a second amino acid.

The term "peptide backbone" means the chain of atoms of a peptide comprising the carboxamide groups that are the peptide bonds together with the atoms of the amino acids that link the carboxyl and amino groups of the amino acid (usually the α-carbon of an α-aminoacid).

The term "side chain" means groups that are attached to the peptide backbone, and typically refers to the group attached to the α-carbon of an α-amino acid. For example, for the side chains of the proteinogenic amino acids include: methyl (alanine), hydroxymethyl (serine), benzyl (phenylalanine), mercaptomethyl (cysteine), and carboxymethyl (aspartic acid).

The term "derivative" as applied to compounds comprising a peptide chain means a compound wherein one or more of the amino, hydroxyl, or carboxyl groups in a side chain of the peptide, or the terminal amino or carboxyl groups, is modified to a derivative functional group. An amino group may be derivatized as an amide (such as an alkyl carboxamide, acetamide), a carbamate (such as an alkyl carbamate, e.g. methyl carbamate or t-butylcarbamate), or a urea. A hydroxyl group may be derivatized as an ester (such as an alkanoate, e.g. acetate, propionate, or an arenecarboxylate, e.g. benzoate), a carbamate (such as an alkyl carbamate, e.g. methyl carbamate), a carbonate (such as an alkyl carbonate, e.g. ethyl carbonate. A carboxyl group may be derivatized as an ester (such as an alkyl ester, e.g. ethyl ester) or an amide (e.g. primary carboxamide, an N-alkyl secondary carboxamide, or an N,N-dialkylcarboxamide). The person skilled in the art will appreciate that derivatives of the peptide will be expected to result in retention of the properties of the parent peptide, either because the incorporation of the derivative group does not change the properties of the peptide, or the derivatizing group is removed in vivo (e.g. via metabolism). Preferred embodiments of the invention are those wherein three or fewer of the amino, carboxyl, and hydroxyl groups, and preferably two or fewer, or one or none, are modified to a derivative functional group. The term "derivative" also includes salts, includes salts of derivatives.

The term "terminal derivative" used in reference to a peptide means a peptide where the C-terminal carboxylate group, or the N-terminal amino group, or both is modified to a derivative functional group. The C-terminal carboxyl group may be derivatized as an ester (such as an alkyl ester, e.g. ethyl ester) or an amide (e.g. primary carboxamide, an N-alkyl secondary carboxamide, or an N,N-dialkylcarboxamide). The N-terminal amino group may be derivatized as an ester (such as an alkyl ester, e.g. ethyl. ester) or an amide (e.g. primary carboxamide, an N-alkyl secondary carboxamide, or an N,N-dialkylcarboxamide). The C-terminal carboxyl group and/or the N-terminal amino group may also be in the form of a salt.

The term "isolated compound" means a compound substantially free of contaminants or cell components with which the compound naturally occur, or the reagents used in synthesis or the byproducts of synthesis. "Isolated" and "substantially free of contaminants" does not mean that the preparation is technically pure (homogeneous), but it is sufficiently pure to provide the peptide or polypeptide in a form in which it can be used therapeutically.

The term "protein transduction domain" also called a "cell-penetrating peptide" is used to indicate a peptide, or derivative thereof, that is capable of crossing cell membranes and of directing the transport of a peptide, protein, or molecule associated with the protein transduction domain, from the outside of a cell into the cytoplasm of the cell through the cytoplasmic membrane of the cell.

The term "conjugated" referring to the linking of two peptides means that the two peptides are covalently linked to one another. The linking may be accomplished directly, through the formation of an amide bond between the carboxyl group of one peptide and an amino group of the other peptide, or by means of a linking group wherein the linking group has covalent bonds to each of the peptides. For example, the linking group may be a peptide chain, an amino acid, or any group having at least two functional groups and capable of forming covalent bond to each of the two peptide chains.

The term "HIV-1 therapeutic compound" means any compound that is useful in the treatment or prevention of HIV-infection, including compounds currently used for the treatment or prevention of HIV-infection, investigational compounds for use in the treatment or prevention of HIV-infection, and compounds considered by the person skilled in the art to be useful for the treatment or prevention of HIV-infection.

The term "acquired immune deficiency syndrome therapeutic compound" means any compound that is useful in the treatment or prevention of acquired immune deficiency syndrome, including compounds currently used for the treatment or prevention of acquired immune deficiency syndrome, investigational compounds for use in the treatment or prevention of acquired immune deficiency syndrome, and compounds considered by the person skilled in the art to be useful for the treatment or prevention of acquired immune deficiency syndrome.

The term "directly bound", referring to the joining of two chemical groups, means that the groups are linked by means of a covalent bond (rather than being linked by virtue of each being bound to a linking group).

The term "Vif antagonist" means a molecule that binds to Vif protein, preferably, the multimerization domain within Vif protein, thereby inhibiting Vif-Vif interaction and Vif protein multimerization.

The term "tissue culture infectious dose 50" (or "$TCID_{50}$") means that quantity of an infectious agent, for example a virus, that when inoculated onto a number of susceptible tissue cultures will infect 50% of the individual cultures.

II. Compounds of the Invention

As one aspect of the invention, there is provided a compound of the formula I:

$$X^1\text{-M-SEQ ID NO:1} \quad (I)$$

or a derivative thereof, wherein:

$X^1$-M- represents an optional group comprising a protein transduction domain conjugated to the N-terminus of the amino acid sequence SEQ ID NO:1, wherein:

$X^1$ represents the protein transduction domain; and

-M- represents a single bond or an optional linking group forming a covalent linkage between the protein transduction domain and the peptide consisting of the amino acid sequence SEQ ID NO:1;

provided that if the compound comprises an amino acid directly bound to the N-terminus of the amino acid sequence SEQ ID NO:1 then the amino acid directly bound to the N-terminus is other than asparagine.

When it is stated that "$X^1$-M- represents an optional group" it is meant that the formula I is intended to encompass both a compound of the formula $X^1$-M-SEQ ID NO:1, or a derivative thereof, where the amino acid sequence SEQ ID NO:1 is conjugated to a protein transduction domain as well as the peptide consisting of the amino acid sequence SEQ ID NO:1, or a derivative thereof which is not conjugated to a protein transduction domain.

a. Linking Groups

In the case where the peptide of the amino acid sequence SEQ ID NO:1 is conjugated to a protein transduction domain, the link between the peptide of the amino acid sequence SEQ ID NO:1 and the protein transduction domain is formed via a single bond or an optional linking group. Since the purpose of the linking group is merely to covalently join the protein transduction domain and the peptide of amino acid sequence SEQ ID NO:1, the person skilled in the art will be able a large number of ways in which to achieve such linkage. In essence the linking group may be any moiety that is at least bifunctional provided that the resulting link between the protein transduction domain and the amino acid sequence SEQ ID NO:1 is stable. Suitable linking moieties include bi- and multi-functional alkyl, aryl, aralkyl or peptidic moieties, alkyl, aryl, or aralkyl aldehydes acids esters and anhydrides, sulfhydryl or carboxyl groups, such as maleimido benzoic acid derivatives, maleimido propionic acid derivatives and succinimido derivatives or may be derived from cyanuric bromide or chloride, carbonyldiimidazole, succinimidyl esters or sulphonic halides and the like (Fischer et al., U.S. Pat. No. 6,472,507, the entire disclosure of which is incorporated herein by reference). The functional groups on the linker moiety may include amino, hydrazino, hydroxyl, thiol, maleimido, carbonyl, and carboxyl groups. Optionally the linker group is selected so as to be sufficiently labile (e.g., to enzymatic cleavage by an enzyme present in the targeted tissue) so that it is cleaved following transport of the peptide of the amino acid sequence SEQ ID NO:1 thereby, releasing the peptide. Exemplary labile linkages are described in Low et al., U.S. Pat. No. 5,108,921, the entire disclosure of which is incorporated herein by reference. The peptide-active agent delivery system may also dissociate by way of chemical cleavage between the active agent and peptide of the invention. Within the embodiments wherein the linker moiety includes amino acid residues, such cleavage may occur within the linker moiety itself.

The examples provided below are intended to be illustrative and not comprehensive. Thus, the examples below illustrate the case where the bonds between the -M- group and the peptides are amide bonds, but the person skilled in the art would appreciate that the link may be formed by means of any functional groups capable of forming bonds between the terminal —NH— group of the amino acid sequence SEQ ID NO:1 and a —C(=O)— group of the terminal (or other) carboxyl group (or the terminal, or other —NH— group, or any other functional group of the protein transduction domain).

If the link formed by the linking group is between the amino acid terminus of the peptide of the amino acid sequence SEQ ID NO:1 and a carboxyl group of the protein transduction domain (for example the terminal carboxyl group) any amino acid (including, but not restricted to, α-amino acids including, but not restricted to, the proteinogenic amino acids) or a peptide chain may form the link between the peptide of the amino acid sequence SEQ ID NO:1 is conjugated to a protein transduction domain.

Examples of suitable linking groups -M- for linking the N-terminus of the amino acid sequence SEQ ID NO:1 and a carboxyl group of the protein transduction domain include:

—NH—CH(R)—C(=O)—, wherein R is a side chain of a proteinogenic amino acid;
a peptide chain; and
—NH—X$_m$—C(=O)—, wherein:
  m is one or greater, preferably one to three,
  each —X— is selected from the group consisting of
    a linear, branched, or cyclic aliphatic hydrocarbon, wherein one or more methylene groups are optionally replaced by —O— or —S— and one or more methine groups are optionally replaced by N;
    —CH$_2$CH$_2$(OCH$_2$CH$_2$)$_n$—; wherein n is one or greater;
    and an aromatic or heteroaromatic ring.

If the link formed by the linking group is between the amino acid terminus of the peptide of the amino acid sequence SEQ ID NO:1 and an amino group of the protein transduction domain (for example the terminal amino group) the link between the two peptide groups could be, for example be a urea (where -M- is —C(=O)—) or any dicarboxylic acid residue (e.g. -M- is —C(=O)—(C$_1$-C$_6$)alkylene-C(=O)—).

Examples of suitable lining group -M- for linking the N-terminus of the amino acid sequence SEQ ID NO:1 and an amino group of the protein transduction domain include:
—C(=O)— (i.e. a urea);
—C(=O)-Pep$^1$—NH—C(=O)—NH-Pep$^2$—C(=O)—, wherein —NH-Pep$^1$—C(=O)— and —NH—Pep$^2$—C(=O)— each represent either an amino acid or a peptide chain, linked via their amino termini (or the α-amino group in the case of an amino acid) by the urea linkage —NH—C(=O)—NH—; and
—C(=O)—X$_m$—C(=O)—, wherein:
  m is one or greater, preferably one to three,
  each —X— is selected from the group consisting of
    a linear, branched, or cyclic aliphatic hydrocarbon, wherein one or more methylene groups are optionally replaced by —O— or —S— and one or more methine groups are optionally replaced by N;
    —CH$_2$CH$_2$(OCH$_2$CH$_2$)$_n$—; wherein n is one or greater;
    and an aromatic or heteroaromatic ring.

Although the -M- group is referred to as "linking" the protein transduction domain and the amino acid sequence SEQ ID NO:1, the use of this term is not intended to imply any limitation as to the process by which the compound of formula I is synthesized. Thus it is not necessary that the protein transduction domain and a peptide of amino acid sequence SEQ ID NO:1 be separately synthesized and then linked together. Rather the term merely describes the structural connection between of the protein transduction domain, the amino acid sequence SEQ ID NO:1, and the linking group. -M- in the compound of formula I.

b. Protein Transduction Domains

A protein transduction domain is a peptide that is capable of crossing cell membranes and of directing the transport of a peptide, protein, or molecule associated with the protein transduction domain; from the outside of a cell into the cytoplasm of the cell through the cytoplasmic membrane of the cell.

Several naturally occurring proteins have been able to enter cells easily, including the TAT protein of HIV, the antennapedia protein from *Drosophila*, and the VP22 protein from the herpes simplex virus. Although the mechanism of cellular entry for such proteins is not fully understood, it has been found that relatively short sequences (a protein transduction sequence or a membrane fusion sequence) in such proteins accounts for the facile cellular entry. The property of promoting facile cellular entry is retained even when the peptide sequence is conjugated to another molecule. As a result, conjugation to such sequences can be used to facilitate delivery into cells of other molecules.

Protein transduction domains have been the subject of considerable interest and investigation because of their ability, through conjugation to other compounds, to facilitate transport of the conjugated compound into the cell, and as a result a substantial body of literature has been published. See, for example, *Handbook of Cell-Penetrating Peptides*, by Ulo Langel (Editor) (CRC Press, 2$^{nd}$ Edition, 2006). *Cell-Penetrating Peptides: Process and Applications*, by Ulo Langel (Editor) (CRC Press, 1$^{st}$ Edition, 2002); E. L Snyder, et al., "Cell-penetrating Peptides in Drug Delivery", *Pharm. Res.*, 2004, 21(3), 389-93. A. J. M. Beerens, et al., "Protein Transduction Domains and their utility in Gene Therapy", *Current Gene Therapy*, 2003, 3(5), 486-94; F. Hudecz, et al., "Medium-sized peptides as built in canriers for biologically active compounds", *Med. Res. Rev.*, 2005, 25(6), 679-736.

Examples of amino acid sequences that may be incorporated in, or used as, protein transduction domains are those shown in Table 2.

TABLE 2

Examples of Protein transduction domains

| Sequence | Name and/or Source |
|---|---|
| Tyr Gly Arg Lys Lys Arg Arg Gln Arg Arg Arg Gly (SEQ ID NO: 4) | HP/TAT |
| Gly Arg Lys Lys Arg Arg Gln Arg Arg Arg Pro Pro Gln Cys (SEQ ID NO: 5) | HIV TAT |
| Gly Arg Lys Lys Arg Arg Gln Arg Arg Arg Pro Pro Gln (SEQ ID NO: 6) | HIV TAT |
| Tyr Gly Arg Lys Lys Arg Gln Arg Arg (SEQ ID NO: 7) | HIV TAT |
| Tyr Ala Arg Lys Ala Arg Arg Gln Ala Arg Arg (SEQ ID NO: 8) | Synthetic sequence (based on HIV TAT) |
| Tyr Ala Arg Ala Ala Ala Arg Gln Ala Arg Ala (SEQ ID NO: 9) | Synthetic sequence (based on HIV TAT) |
| Tyr Ala Arg Ala Ala Arg Arg Ala Ala Arg Arg (SEQ ID NO: 10) | Synthetic sequence (based on HIV TAT) |

TABLE 2-continued

Examples of Protein transduction domains

| Sequence | Name and/or Source |
|---|---|
| Tyr Ala Arg Ala Ala Arg Arg Ala Ala Arg Ala<br>(SEQ ID NO: 11) | Synthetic sequence<br>(based on HIV TAT) |
| Arg Gln Ile Lye Ile Trp Phe Gln Asn Arg Arg Met Lys<br>Trp Lys Lys<br>(SEQ ID NO: 12) | Pantp (43-88) ("Penetratin") |
| Lys Lye Trp Lys Met Arg Arg Asn Gln Phe Trp Val Lys<br>Val Gln Arg<br>(SEQ ID NO: 13) | Retro-inverso pAntp (43-48) |
| Arg Arg Trp Arg Arg Trp Trp Arg ArgTrp Trp Arg Arg<br>Trp Arg Arg<br>(SEQ ID NO: 14) | W/R Penetratin |
| Arg Arg Met Lys Trp Lys Lys<br>(SEQ ID NO: 15) | Pantp (52-58) |
| Arg Arg Arg Arg Arg Arg Arg<br>(SEQ ID NO: 16) | Arginine 7-mer |
| Arg Arg Arg Arg Arg Arg Arg Arg Arg<br>(SEQ ID NO: 17) | Arginine 9-mer |
| Asp Ala Ala Thr Arg Ser Ala Ala Ser Arg Pro Thr Gln<br>Arg Pro Arg Ala Pro Ala Arg Ser Ala Ser Arg Pro Arg<br>Arg Pro Val Glu<br>(SEQ ID NO: 18) | VP22 transduction domain (Herpes<br>Simplex Virus I) |
| Gly Ala Leu Phe Leu Gly Trp Len Gly Ala Ala Gly Ser<br>Thr Met Gly<br>(SEQ ID NO: 19) | GP41 fusion sequence |
| Gly Ala Leu Phe Leu Gly Phe Leu Gly Ala Ala Gly Ser<br>Thr Met Gly Ala Trp Ser Gln Pro Lys Ser Lys Arg Lys<br>Val<br>(SEQ ID NO: 20) | GP41 fusion sequence. |
| Met Gly Len Gly Leu His Leu Leu Val Leu Ala Ala Ala<br>Leu Gln Gly Ala Trp Ser Gln Pro lys Lys Lys Arg Lys<br>Val<br>(SEQ ID NO: 21) | Caiman crocodylus Ig(v) light chain-<br>SN40NLS |
| Pro Leu Ser Ser Ile Phe Ser Arg Ile Gly Asp Pro<br>(SEQ ID NO: 22) | Hepatitis B virus PreS2 antigen<br>consisting of the translocation motif<br>from residues 41-52. |
| Phe Trp Arg Gly Asp Leu Val Phe Asp Phe Gln Val<br>(SEQ ID NO: 23) | Hepatitis A virus VP3 core protein. |
| Lys Phe Thr Ile Val Phe Pro His Asn Gln Lys Gly Asn<br>Trp Lys Asn Val Pro Ser Asn Tyr His Tyr Cys Pro<br>(SEQ ID NO: 24) | Vesicular stomatitis virus VSV-G<br>peptide. |
| Ala Lys Arg Ala Arg Leu Ser Thr Ser Phe Asn Pro Val<br>Tyr Pro Tyr Glu Asp Glu Ser<br>(SEQ ID NO: 25) | Adenovirus fiber |
| Gly Trp Thr Leu Asn Ser Ala Gly Tyr Leu Leu Gly Lys<br>Ile Asn Leu Lys Ala Leu Ala Ala Leu Ala Lys Lys Ile<br>Leu<br>(SEQ ID NO: 26) | Transportan |
| Arg Gly Gly Arg Leu Ser Tyr Ser Arg Arg Arg Phe Ser<br>Thr Ser Thr Gly Arg<br>(SEQ ID NO: 27) | SynB1 |
| Ala Ala Val Ala Leu Leu Pro Ala Val Leu Leu Ala Leu<br>Leu Ala Pro<br>(SEQ ID NO: 28) | Kaposi's sarcoma-associated<br>herpesvirus Kaposi FGF signal<br>sequence |
| Ala Ala Val Leu Leu Pro Val Leu Leu Ala Ala Pro<br>(SEQ ID NO: 29) | Kapos's sarcoma-associated<br>herpesvirus Kaposi FGF signal<br>sequence |

TABLE 2-continued

Examples of Protein transduction domains

| Sequence | Name and/or Source |
|---|---|
| Val Thr Val Len Ala Leu Gly Ala Leu Ala Gly Val Gly Val Gly (SEQ ID NO: 30) | Human integrin beta3 signal sequence |
| Val Ala Tyr Ile Ser Arg Gly Gly Val Ser Thr Tyr Tyr Ser Asp Thr Val Lys Gly Arg Phe Thr Arg Gln Lys Tyr Asn Lys Arg Ala (SEQ ID NO: 31) | P3 Membrane Fusion Sequence |
| Lys Leu Ala Leu Lys Leu Ala Leu Lys Ala Leu Lys Ala Ala Leu Lys Leu Ala (SEQ ID NO: 32) | Model ambiphilic peptide |
| Trp Glu Ala Lys Leu Ala Lys Ala Leu Ala Lys Ala Leu Ala Lys His Leu Ala Lys Ala Leu Ala Lys Ala Leu Lys Ala Cys Gln Ala (SEQ ID NO: 33) | KALA |
| Arg Arg Gln Arg Arg Thr Ser Lys Leu Met Lys Arg (SEQ ID NO: 34) | Synthetic (U.S. Pat. No. 6,881,825) | c. Particular and Preferred Embodiments of the Compounds of the Invention

Preferred embodiments of the compounds of the invention are those wherein -M- consists of a single bond, an amino acid or a peptide. Where -M- consists of an amino acid, the amino acid is preferably glycine. Where -M- consists of a peptide, the peptide is preferably linked via its C-teminus to the amino-terminus of the peptide of amino acid sequence SEQ ID NO:1 and via its N-terminus to the C-temiunus of the protein transduction domain. The peptide also preferably consists often amino acid residues or fewer.

In some embodiments, the compound of formula I comprises the amino acid sequence SEQ ID NO:3.

In some embodiments, the protein transduction domain is directly linked at its C-terminus to -M-.

In some embodiments, the protein transduction domain comprises and optionally consists of an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34, preferably SEQ ID NO:4, SEQ ID NO:5, SEQ ID NO:6, SEQ ID NO:7, SEQ ID NO:8, SEQ ID NO:9,:SEQ ID NO:10, or SEQ ID NO:11, most preferably SEQ ID NO: 4.

In particular embodiments, the compound of formula I is a peptide consisting of an amino acid sequence selected from the group consisting of SEQ ID NO:1, SEQ ID NO:2, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73.

In a preferred embodiment, the compound of formula I is a peptide consisting of an amino acid sequence SEQ ID NO:1.

In another preferred embodiment, the compound of formula I is a peptide consisting of an amino acid sequence SEQ ID NO:2.

In other preferred embodiments the compound of formula I, or any of the embodiments thereof, is an isolated compound. In other preferred embodiments, the compound of formula I, and compositions containing the compound, including pharmaceutical compositions, is substantially free of pharmaceutically unacceptable contaminants. A pharmaceutically unacceptable contaminant is a compound which, if present in more than an insubstantial amount, would render the compound unsuitable for use as a pharmaceutical for therapeutic-administration to a human being.

III. Preparation of Compounds of the Invention

The compounds of the invention may be prepared by methods known to the person skilled in the art of peptide and organic synthesis.

Peptides of the present invention may be recombinant peptides or synthetic peptides. They may also be chemically synthesized, using, for example, solid phase synthesis methods. The protein transduction domains may be natural peptides or synthetic and may be prepared by isolation from natural sources or may be synthesized.

The peptides of the present invention may be synthesized de novo using peptide synthesis methods. In such methods, the peptide chain is prepared by a series of coupling reactions in which the constituent amino acids are added to the growing peptide chain in the desired sequence. The use of various N-protecting groups, e.g., the carbobenzyloxy group or the t-butyloxycarbonyl group; various coupling reagents e.g., dicyclohexylcarbodiimide or carbonyldiimidazole; various active esters, e.g., esters of N-hydroxyphthalimide or N-hydroxy-succinimide; and the various cleavage-reagents, e.g., trifluoroacetic acid (TFA), HCl in dioxane, boron tris-trifluoracetate) and cyanogen bromide; and reaction in solution with isolation and purification of intermediates are methods well-known to those of ordinary skill in the art. The reaction may be carried out with the peptide either in solution or attached to a solid phase support. In the solid phase method, the peptide is released from the solid phase support following completion of the synthesis.

The preferred peptide synthesis method follows Merrifield solid-phase procedures. See Merrifield, *J. Am. Chem. Soc.,* 1963, 85, 2149-54 and Science, 1965, 50, 178-85. Additional information about the solid phase synthesis procedure can be had by reference to the treatises *Solid Phase Peptide Synthesis: A Practical Approach* by E. Atherton and R. C. Sheppard (Oxford University Press, 1989, *Solid phase peptide synthesis,* by J. M. Stewart and J. D. Young, (2nd edition, Pierce Chemical Company, Rockford, 1984), and the review chapters by R. Merrifield in *Advances in Enzymology* 32:221-296, edited by F. F. Nold (Interscience Publishers, New York, 1969) and by B. W. Erickson and R. Merrifield in *The Proteins* Vol. 2, pp. 255 et seq., edited by Neurath and Hill, (Academic Press, New York, 1976.

The synthesis of peptides by solution methods is described in The Proteins, Vol. 11, edited by Neurath et al. ($3^{rd}$ Edition, Academic Press 1976). Other general references to the synthesis of peptides include: *Peptide Synthesis Protocols*, edited by M. W. Pennington and Ben M. Dunn (Humana Press 1994), *Principles of Peptide Synthesis*, by Miklos Bodanszky ($2^{nd}$ edition, Springer-Verlag, 1993), and *Chemical Approaches to the Synthesis of Peptides and Proteins* by Paul Lloyd-Williams, F. Albericio, E. Giralt (CRC Press 1997), and *Synthetic Peptides: A User's Guide;* edited by G. Grant (Oxford University Press, 2002).

Compounds of formula I wherein the linker -M- is other than a peptide chain may be prepared, for example, by coupling the protein transduction domain and the suitable linking molecule using methods that will vary according to the exact nature of the compound but will be apparent to the person skilled in the art. Suitable protecting group strategies may be employed in order to achieve the desired selectivity of the site of coupling, as described, for example, in *Protective Groups in Organic Synthesis*, by T. W. Greene and P. G. M. Wuts ($3^{rd}$ Edition, Wiley 1999)

Alternatively, the peptides may be prepared utilizing recombinant DNA technology, which comprises combining a nucleic acid encoding the peptide thereof in a suitable vector, inserting the resulting vector into a suitable host cell, recovering the peptide produced by the resulting host cell, and purifying the polypeptide recovered. The techniques of recombinant DNA technology are known to those of ordinary skill in the art. General methods for the cloning and expression of recombinant molecules are described in *Molecular Cloning* by Maniatis (Cold Spring Harbor Laboratories, 1982), *Molecular Cloning* by Sambrook (Cold Spring Harbor Laboratories, Second Ed., 1989), and in *Current Protocols in Molecular Biology* by Ausubel (Wiley and Sons, 1987).

The nucleic acid encoding the desired peptides may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate in which they are administered. Selection of the appropriate regulatory region or regions is a routine matter, within the level of ordinary skill in the art.

Promoters that may be used in the synthesis of compounds of the present invention include both constitutive promoters and regulated (inducible) promoters. The promoters may be prokaryotic or eukaryotic depending on the host. Among the prokaryotic (including bacteriophage) promoters useful for practice of this invention are lac, T3, T7, lambda-Pr' Pl' and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells), promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S. Pat. No. 5,168,062 and U.S. Pat. No. 5,385,839, the entire disclosures of which are incorporated herein by reference.

Examples of polyadenylation signals that can be used in the present invention include, but are not limited to, SV40. polyadenylation signals and LTR polyadenylation signals.

The compounds of the invention, whether prepared by chemical synthesis or recombinant DNA technology may be purified using known techniques, for example preparative HPLC. The compounds may then be assayed for biological activity according to the assay methods described herein, as well as by methods known to those of skill in the art.

IV. Biological Evaluation of the Compounds of the Invention

Molecules that bind to Vif or Vif conjugate and inhibit Vif protein multimerization may be assayed using a Vif-Vif binding assay. More specifically, Vif-Vif binding assay comprises the steps of 1) conjugating Vif or Vif-containing peptides to a column or beads; 2) applying a test molecule and labeled Vif, or fragments thereof, that contains the multimerization domain on the Vif- or Vif-containing peptide-conjugated column or beads; 3) washing the column or beads and dissociating the labeled Vif, or fragments thereof, from the column or beads; and 4) measuring and comparing the amount of labeled Vif, or fragments thereof, that was bound to the column or beads to determine the antagonism activity of the molecule. "Labeled Vif or fragments thereof," refers to, but is not limited to, radio labeled, chemical labeled, or fluorescent labeled Vif. The screening is preferably performed using $^{35}$S-labeled Vif.

The effectiveness of compounds in inhibiting Vif function may be determined by assaying the effectiveness of the compounds in inhibiting Vif-mediated reduction of cellular hA3G levels. Suitable cells, such as H9, HEK 293T or MT-2 cells, are transfected with a gene construct comprising hA3G conjugated with enhanced green fluorescent protein (EGFP) are infected with virus and the presence of EGFP-hA3G fluorescence is monitored using fluorescence microscopy or fluorescence detection by an ELISA plate reader. The effectiveness of a compound in reducing Vif-mediated reduction in hA3G levels upon infection with virus can thereby be measured.

The effectiveness of compounds in inhibiting Vif function may also be determined by assaying hA3G in virons. Virons released from virus infected cells that express hA3G will have high levels of hA3G if Vif function is inhibited, whereas functional Vif leads to the destruction of hA3G and blocks incorporation of Vif into virons. Thus, drugs that are effective in blocking Vif function will result in high hA3G levels in virons. Virons released from cells may be assayed for their hA3G content by sodium dodecyl sulfate polyacrylamide gel electrophoresis (SDS-PAGE) of the virons, western blotting the resulting gel, and probing the blot with hA3G antibodies. If the blots are also probed with an antibody to another viral protein, such as p24, the measured hA3G abundance can be normalized to account for variations in the viral load (i.e. expressed as per unit viral load).

Compounds identified as binding to Vif may be tested for activity in in vitro and in vivo antiviral assays known to the person skilled in the art, for example as described herein. The following example describes an illustrative procedure for evaluating a compound for efficacy versus HIV-1.

The effect of the therapeutic on HIV-1 replication in cultured cells may first be determined. This may be performed, for example by acutely infecting hematopoietic cells (e.g., MT-2 T-cell lymphoma cells, primary peripheral blood mononuclear cells (PBMCs), isolated macrophages, isolated CD4-positive T cells or cultured H9. human T cells) with HIV-1 using titers known in the art to acutely infect cells in vitro, such as $10^{4,5}$ TCID$_{50}$/mL. The cells are then cultured in the presence of varying amounts of a test compound. Cultures are then assayed for HIV-1 production (e.g. by measuring levels of reverse transcriptase using a reverse transcriptase assay, or p24 antigen using a commercially available ELISA assay). Reduction in viral levels over levels observed in untreated controls indicates the test compound is effective in vitro for treatment of HIV-1 infection.

Prior to testing in humans, the test compound is preferably tested in animal models of HIV-1 infection. In one such model, the compound of the invention is administered to mice transgenic for HIV-1, e.g., mice which have integrated molecular clone pNL4-3 containing 7.4 kb of the HIV-1 proviral genome deleted in the gag and pol genes (P. Dickie, et al., *Virology*, 1991, 185, 109-119). Skin biopsies taken from the mice are tested for HIV-1 gene expression by RT-PCR (reverse transcription-polymerase chain reaction) or for HIV-1 antigen expression, such as expression of gp120 or NEF, by immunostaining. Additionally, the mice are examined for reduction in the cachexia and growth retardation usually observed in HIV-1 transgenic mice (R. R. Franks, et al., *Pediatric Res.*, 1995, 37, 56-63).

The efficacy of compounds of the invention can also be determined in SIV infected rhesus monkeys (N. L. Letrin, et al., *J. AIDS*, 1990, 3, 1023-40), particularly rhesus monkeys infected with SIV$_{mac251}$, which induces a syndrome in experimentally infected monkeys which is very similar to human AIDS (H. Kestler, et al., *Science*, 1990, 248, 1109-12). Specifically, monkeys can be infected with cell free SIV$_{mac251}$, for example, with virus at a titer of $10^{4.5}$ TCID$_{50}$/mL. Infection is monitored by the appearance of SIV p27 antigen in PBMCs. Utility of the compound of the invention is characterized by normal weight gain, decrease in SIV titer in PBMCs and an increase in CD4 positive T cells.

In order to determine the efficacy of the compounds in vivo on HIV-infected human cells hollow fiber assays may be used. HIV-infected human cells are grown in hollow fibers implanted in experimental animals, such as the SCID mouse, and the spread of infection from the cells is monitored using end points such as PCR, flow cytometry, p24, or reverse transcriptase. See, e.g., B. Taggart, et al., *Antiviral Res.*, 2004, 63(i), 1-6.

In human subjects, the efficacy of treatment with a compound may be determined by measuring various parameters of HIV-1 infection and HIV-1 associated disease. Specifically, the change in viral load can be determined by quantitative assays, for plasma HIV-1 RNA using quantitative RT-PCR (B. Van Gemen, et al., *J. Virol. Methods*, 1994, 49, 157-68; Y. H. Chen, et al. *AIDS*, 1992, 6, 533-39) or by assays for viral production from isolated PBMCs. Viral production from PBMCs is determined by co-culturing PBMCs from the subject with H9 cells and subsequent measurement of HIV-1 titers using an ELISA assay for p24 antigen levels (M. Popovic, et al., *Science*, 1984, 204, 497-500). Another indicator of plasma HIV-1 levels and AIDS progression is the production of inflammatory cytokines such as IL-6, IL8 and TNFα; thus, efficacy of the compound of the invention can be assessed by ELISA tests for reduction of serum levels of any or all of these cytokines. The effect of treatment can also be demonstrated by assessing changes in CD4 positive T cell levels, body weight, or any other physical condition associated with HIV infection or AIDS or AIDS Related Complex (ARC).

V. Salts of Compounds of the Invention

Peptide chains typically contain acidic or basic groups (such as amine or carboxyl groups) such groups will not necessarily be in the free base form. When referring to compounds that are peptides or compounds that contain peptide chains the reference is intended to include salt forms of the peptide. Within the scope of the invention, therefore, are salts of the compound of formula I and the derivatives thereof. The preferred salts are pharmaceutically-acceptable salts.

The term "salts" embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound according to Formula I by reacting, for example, the appropriate acid or base with the compound according to Formula I.

VI. Pharmaceutical Compositions

The compounds of the invention may be administered in the form of a pharmaceutical composition, in combination with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th -Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions are preferably formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects, and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566, describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

Compositions of the compounds of the invention that are suitable for administration intranasally or by inhalation are of particular interest.

The compounds of the invention can be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulae, with or without the use of a suitable propellant, such as dichlorofluoromethane.

The pressurized container, pump, spray, atomizer, or nebulae contains a solution or suspension of the active compound comprising, for example, ethanol (optionally, aqueous ethanol) or a suitable alternative agent for dispersing, solubilizing, or extending release of the active, the propellant(s) as solvent and an optional surfactant, such as sorbitan trioleate or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation may comprise the compound of the invention, propylene glycol, sterile water, ethanol and sodium chloride. Alternative solvents which may bemused instead of propylene glycol include glycerol and polyethylene glycol.

Capsules, blisters and cartridges (made, for example, from gelatin or HPMC) for use in an inhaler or insufflator may be formulated to contain a powder mix of the nicotinamide derivative of formula (I), a suitable powder base such as lactose or starch and a performance modifier such as L-leucine, mannitol, or magnesium stearate.

Formulations for inhaled/intranasal administration may be formulated to be immediate and/or modified release. Modified release formulations include delayed-, sustained-, pulsed-, controlled dual-, targeted and programmed release. Sustained or controlled release can be obtained by using for example poly(D,L-lactic-co-glycolic acid).

VII. Methods of Treatment using Compounds of the Invention

The compounds of the invention inhibit Vif multimerization, and thus can be used for the treatment or prophylaxis of diseases and conditions involving lentivirus infection, as well as other disorders associated with the multimerization of Vif. The process comprises administering an effective amount of the compound, or a pharmaceutical composition comprising the compound, as described herein, to an individual in need of such treatment or prophylaxis. An individual who is in need of such treatment is an individual who is infected with a lentivirus, or suffering from a disorder associated with the multimerization of Vif. An individual who is in need of such prophylaxis is an individual who is at risk of infection with a virus due to actual or suspected exposure to the virus.

In specific embodiments, the compounds are administered therapeutically (including prophylactically): (1) in diseases, disorders, or conditions involving lentiviruses, specifically HIV-1; or (2) in diseases, disorders, or conditions wherein in vitro (or in vivo) assays indicate the utility of Vif antagonist administration. The presence of HIV-1 can be readily detected by any means standard in the art, e.g., by obtaining a patient blood sample and assaying it in vitro for the presence of HIV-1.

Prophylaxis is indicated in previously uninfected individuals after known or suspected acute exposure to an HIV virus. Examples of such prophylactic use of the peptides may include, but are not limited to, prevention of virus transmission from mother to infant and other settings where the likelihood of HIV transmission exists, such as, for example, accidents in health care settings wherein workers are exposed to HIV-containing blood products.

The amount of the therapeutic of the invention that will be effective in the treatment of a particular disorder or condition will depend on the nature of the disorder or condition, is and is determined by standard clinical techniques. In addition, in vitro assays may optionally be employed to help identify optimal dosage ranges. The precise dose to be employed in the formulation also will depend on the route of administration and the seriousness of the disease, disorder, or condition and is decided according to the judgment of the practitioner and each patient's circumstances.

Also provided are methods of treatment or prophylaxis of HIV-1 infection and/or AIDS by the administration of a combination of drugs. The method comprises administering an effective amount of the compound, or a pharmaceutical composition comprising the compound, as described herein, in combination with one or more compounds selected from the group consisting of reverse transcriptase inhibitors, HIV-1 protease inhibitors, or fusion inhibitors (collectively referred to below as "conventional HIV drug") to an individual in need of such treatment or prophylaxis.

For marketed conventional HIV-1 drugs, suitable doses and dosing protocols are recommended by the manufacturer and published, for example in the *Physician's Desk Reference*, 60th Edition (Thomson Healthcare, 2006), the entire disclosure of which is incorporated herein by, reference. For both marketed drugs and investigational chemotherapeutic agents, suitable doses are recommended and published in the literature, in reports of clinical trials of the compounds. The person skilled in the art will refer to such sources in determining a suitable dosed dosing protocol for any particular indication. Such established protocols are preferred, particularly when the conventional HIV drug is being administered in a separate composition from the compound of Formula I. Thus, in a preferred embodiment, the dosage, formulation, route and schedule of administration of the conventional HIV drug is carried out according to the known protocols for the drug. However, a possible advantage of the using the HIV-1 drug in combination with the compounds of the invention is that it may be possible to use either or both of the compounds at a lower dose than would be possible if the compounds were used separately.

VII. Administration of Compounds of the Invention

The compounds may be administered by any route, including oral, rectal, pulmonary, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Typically it is contemplated that treatment would be given at least once per day, typically once, twice, three times or four times per day with the doses given at equal intervals throughout the day and night in order to maintain a constant presence of the drug in order to suppress the virus and reduce the opportunity for development of resistance.

One or more compounds of the invention may be administered simultaneously, by the same or different routes, or at different times during treatment. The compounds of the invention may also be prescribed to be taken in combination with conventional HIV drugs. When used in such combinations compounds of the invention and conventional HIV drugs may be administered simultaneously, by the same or different routes, or at different times during treatment. The dose of the conventional HIV drug selected will depend on the particular compound being used and the route and frequency of administration. Typically, treatment of the conventional HIV drug will also be given at least once per day, typically once, twice, three times or four times per day with the doses given at equal intervals throughout the day and night, although not necessarily according to the same schedule as the compound of the invention.

The treatment may be carried out for as long a period as necessary. Typically it is contemplated that treatment would be continued indefinitely while the infection persists, although discontinuation might be indicated if the compounds no longer produce a beneficial effect, for example due to development of resistance by the viruses. The treating physician will know how to increase, decrease, or interrupt treatment based on patient response.

The specific dose of a compound according to the invention to obtain therapeutic benefit for treatment of a cellular proliferative disorder will, of course, be determined by the particular circumstances of the individual patient including the size, weight, age and sex of the patient, the nature and stage of the disease, the aggressiveness of the disease, and the route of administration of the compound.

For example, a daily dosage from about 0.02 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. Suitable dosage ranges for intravenous administration are generally about 20-500 micrograms of active compound per kilogram body weight.

Suitable dosage ranges for intranasal or inhaled administration are generally about 0.01 pg/kg body weight to 1 mg/kg body weight. In the case of dry powder inhalers and aerosols, the dosage unit is determined by means of a valve which delivers a metered amount. Units in accordance with the invention are typically arranged to administer a metered dose or "puff" which delivers an appropriate dose. The daily dose which may be administered in a single dose or as divided doses throughout the day.

Suppositories generally contain active ingredient in the range of 0.5% to 10% by weight; oral formulations preferably contain 10% to 95% active ingredient.

Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture; use or sale of pharmaceuticals or biological products, which notice reflects approval by the agency of manufacture, use or sale for human administration.

EXAMPLES

The following non-limiting examples are provided to illustrate the invention.

Examples 1-39

Illustrative Compounds of the Invention

The peptides shown in Table 3 are illustrative of compounds within the scope of the invention.

TABLE 3

Illustrative Compounds of the Invention

| Example | Sequence |
|---|---|
| 1 | Gln Gly Gly Ser Pro Leu Pro Arg Ser Val (SEQ ID NO: 1) |
| 2 | Tyr Gly Arg Lys Lys Arg Arg Gln Arg Gly Gln Gly Gly Ser Pro Leu Pro Arg Ser Val (SEQ ID NO: 2) |
| 3 | Gly Arg Lys Lys Arg Arg Gln Arg Arg Pro Pro Gln Cys Gln Gly Gly Ser Pro Leu Pro Arg Ser Val (SEQ ID NO: 37) |
| 4 | Gly Arg Lys Lys Arg Arg Gln Arg Arg Pro Pro Gln Gln Gly Gly Ser Pro Leu Pro Arg Ser Val (SEQ ID NO: 38) |
| 5 | Tyr Gly Arg Lys Lys Arg Arg Gln Arg Arg Gln Gly Gly Ser Pro Leu Pro Arg Ser Val (SEQ ID NO: 39) |

TABLE 3-continued

Illustrative Compounds of the Invention

| Example | Sequence |
|---|---|
| 6 | Tyr Ala Arg Lys Ala Arg Arg Gln Ala Arg Arg Gln Gly Gly Ser Pro Leu Pro Arg Ser Val (SEQ ID NO: 40) |
| 7 | Tyr Ala Arg Ala Ala Ala Arg Gln Ala Arg Ala Gln Gly Gly Ser Pro Leu Pro Arg Ser Val (SEQ ID NO: 41) |
| 8 | Tyr Ala Arg Ala Ala Arg Arg Ala Ala Arg Arg Gln Gly Gly Ser Pro Leu Pro Arg Ser Val (SEQ ID NO: 42) |
| 9 | Tyr Ala Arg Ala Ala Arg Arg Ala Ala Arg Ala Gln Gly Gly Ser Pro Leu Pro Arg Ser Val (SEQ ID NO: 43) |
| 10 | Gly Arg Lys Lys Arg Arg Gln Arg Arg Pro Pro Gly Gln Cys Gln Gly Gly Ser Pro Leu Pro Arg Ser Val (SEQ ID NO: 44) |
| 11 | Gly Arg Lys Lys Arg Arg Gln Arg Arg Pro Pro Gly Gln Gln Gly Gly Ser Pro Leu Pro Arg Ser Val (SEQ ID NO: 45) |
| 12 | Tyr Gly Arg Lys Lys Arg Arg Gln Arg Arg Gly Gln Gly Gly Ser Pro Leu Pro Arg Ser Val (SEQ ID NO: 46) |
| 13 | Tyr Ala Arg Lys Ala Arg Arg Gln Ala Arg Arg Gly Gln Gly Gly Ser Pro Leu Pro Arg Ser Val (SEQ ID NO: 47) |
| 14 | Tyr Ala Arg Ala Ala Ala Arg Gln Ala Arg Ala Gly Gln Gly Gly Ser Pro Leu Pro Arg Ser Val (SEQ ID NO: 48) |
| 15 | Tyr Ala Arg Ala Ala Arg Arg Ala Ala Arg Arg Gly Gln Gly Gly Ser Pro Lou Pro Arg Ser Val (SEQ ID NO: 49) |
| 16 | Tyr Ala Arg Ala Ala Arg Arg Ala Ala Arg Ala Gly Gln Gly Gly Ser Pro Leu Pro Arg Ser Val (SEQ ID NO: 50) |
| 17 | Arg Gln Ile Lys Ile Trp Phe Gln Asn Arg Arg Met Lys Trp Lys Lys Gln Gly Gly Ser Pro Leu Pro Arg Ser Val (SEQ ID NO: 51) |
| 18 | Lys Lys Trp Lys Met Arg Arg Asn Gln Phe Trp Val Lys Val Gln Arg Gln Gly Gly Ser Pro Leu Pro Arg Ser Val (SEQ ID NO: 52) |
| 19 | Arg Arg Trp Arg Arg Trp Trp Arg Arg Trp Trp Arg Arg Trp Arg Arg Gln Gly Gly Ser Pro Leu Pro Arg Ser Val (SEQ ID NO: 53) |
| 20 | Arg Arg Met Lys Trp Lys Lys Gln Gly Gly Ser Pro Leu Pro Arg Ser Val (SEQ ID NO: 54) |

TABLE 3-continued

Illustrative Compounds of the Invention

| Example | Sequence |
|---|---|
| 21 | Arg Arg Arg Arg Arg Arg Arg Gln Gly Gly Ser Pro Leu Pro Arg Ser Val (SEQ ID NO: 55) |
| 22 | Arg Arg Arg Arg Arg Arg Arg Arg Gln Gly Gly Ser Pro Leu Pro Arg Ser Val (SEQ ID NO: 56) |
| 23 | Asp Ala Ala Thr Arg Ser Ala Ala Ser Arg Pro Thr Gln Arg Pro Arg Ala Pro Ala Arg Ser Ala Ser Arg Pro Arg Arg Pro Val Glu Gln Gly Gly Ser Pro Len Pro Arg Ser Val (SEQ ID NO: 57) |
| 24 | Gly Ala Leu Phe Leu Gly Trp Len Gly Ala Ala Gly Ser Thr Met Gly Gln Gly Gly Ser Pro Leu Pro Arg Ser Val (SEQ ID NO: 58) |
| 25 | Gly Ala Leu Phe Leu Gly Phe Len Gly Ala Ala Gly Ser Thr Met Gly Ala Trp Ser Gln Pro Lys Ser Lys Arg Lys Val Gln Gly Gly Ser Pro Leu Pro Arg Ser Val (SEQ ID NO: 59) |
| 26 | Met Gly Leu Gly Leu His Leu Leu Val Leu Ala Ala Ala Leu Gln Gly Ala Trp Ser Gln Pro Lys Lys Lys Arg Lys Val Gln Gly Gly Ser Pro Leu Pro Arg Ser Val (SEQ ID NO: 60) |
| 27 | Pro Leu Ser Ser Ile Phe Ser Arg Ile Gly Asp Pro Gln Gly Gly Ser Pro Len Pro Arg Ser Val (SEQ ID NO: 61) |
| 28 | Phe Trp Arg Gly Asp Leu Val Phe Asp Phe Gln Val Gln Gly Gly Ser Pro Leu Pro Arg Ser Val (SEQ ID NO: 62) |
| 29 | Lys Phe Thr Ile Val Phe Pro His Asn Gln Lys Gly Asn Trp Lys Asn Val Pro Ser Asn Tyr His Tyr Cys Pro Gln Gly Gly Ser Pro Leu Pro Arg Ser Val (SEQ ID NO: 63) |
| 30 | Ala Lys Arg Ala Arg Leu Ser Thr Ser Phe Asn Pro Val Tyr Pro Tyr Gln Asp Gln Ser Gln Gly Gly Ser Pro Leu Pro Arg Ser Val (SEQ ID NO: 64) |
| 31 | Gly Trp Thr Leu Asn Ser Ala Gly Tyr Leu Leu Gly Lys Ile Asn Len Lys Ala Len Ala Ala Leu Ala Lys Lys Ile Leu Gln Gly Gly Ser Pro Leu Pro Arg Ser Val (SEQ ID NO: 65) |
| 32 | Arg Gly Gly Arg Leu Ser Tyr Ser Arg Arg Arg Phe Ser Thr Ser Thr Gly Arg Gln Gly Gly Ser Pro Leu Pro Arg Ser Val (SEQ ID NO: 66) |
| 33 | Ala Ala Val Ala Leu Leu Pro Ala Val Leu Leu Ala Leu Leu Ala Pro Gln Gly Gly Ser Pro Leu Pro Arg Ser Val (SEQ ID NO: 67) |
| 34 | Ala Ala Val Leu Leu Pro Val Leu Leu Ala Ala Pro Gln Gly Gly Ser Pro Len Pro Arg Ser Val (SEQ ID NO: 68) |
| 35 | Val Thr Val Leu Ala Leu Gly Ala Leu Ala Gly Val Gly Val Gly Gln Gly Gly Ser Pro Leu Pro Arg Ser Val (SEQ ID NO: 69) |
| 36 | Val Ala Tyr Ile Ser Arg Gly Gly Val Ser Thr Tyr Tyr Ser Asp Thr Val Lys Gly Arg Phe Thr Arg Gln Lys Tyr Asn Lys Arg Ala Gln Gly Gly Ser Pro Leu Phr Arg Ser Val (SEQ ID NO: 70) |
| 37 | Lys Leu Ala Leu Lys Leu Ala Leu Lys Ala Leu Lys Ala Ala Leu Lys Leu Ala Gln Gly Gly Ser Pro Leu Pro Arg Ser Val (SEQ ID NO: 71) |
| 38 | Trp Gln Ala Lys Leu Ala Lys Ala Leu Ala Lys Ala Leu Ala Lys His Leu Ala Lys Ala Leu Ala Lys Ala Leu Lys Ala Cys Gln Ala Gln Gly Gly Ser Pro Leu Pro Arg Ser Val (SEQ ID NO: 72) |
| 39 | Arg Arg Gln Arg Arg Thr Ser Lys Leu Met Lys Arg Gln Gly Gly Ser Pro Len Pro Arg Ser Val (SEQ ID NO: 73) |

Example 40

Protein Expression and in vitro Binding Assays

Compounds that bind to Vif may be identified, for example, using an in vitro binding assay. The assay may be performed as described in U.S. Pat. No. 6,653,443, essentially as follows.

The vector pGEX, with or without the vif gene, is transformed into BL21 competent cells (Novagen, Madison, Wis.). After growth at 37° C. to approximately 0.6 O.D., the expression of GST or GST-Vif proteins is induced by 0.4 mM isopropylthio-β-D-galactoside (IPTG). The bacterial cells are lyzed by adding lysing buffer (1% Triton-X-100, 0.1 mg/mL lysozyme, 2 mM EDTA, 1 mM PMSF, 2 µg/mL leupeptin, and 1 µg/mL aprotinin), followed by sonication. The sample was pelleted at 12,000 g for 10 min at 4° C., and the supernatant is applied to a glutathione-conjugated agarose bead (Sigma, St. Louis, Mo.) column. After batch binding, the matrix is washed three times, each time by the addition of 10 bed volumes of phosphorus-buffer saline (PBS). The GST or GST-Vif conjugated agarose beads were then aliquoted and stored at −20° C.

Conversely, $^{35}$S-labeled Vif is synthesized utilizing SPT3 kits (Novagen, Madison, Wis.). The protocol supplied by the manufacturer is followed. After in vitro translation, RNaseA (0.2 mg/mL) is added to stop the reaction and remove tRNAs and the in vitro transcribed mRNA. The trichloroacetic acid (TCA)-insoluble radioactive amino acids were quantitated in the presence of a scintillation cocktail.

For GST pull-down assays, a GST or GST-Vif conjugated bead slurry is mixed with $^{35}$S-labeled Vif in a binding buffer [150 mM NaCl, 20 mM Tris-HCl (pH 7.5), 0.1% Triton-X-100]. After binding at 4° C. for 1 hour, the mixture is centrifuged at 3,000 g for 1 min, and the beads are washed three times with binding buffer. The $^{35}$S-labeled Vif proteins are dissociated from the beads by adding SDS-containing loading buffer and heating at 95° C. for 5 minutes. The samples are then electrophoresized in SDS-PAGE gels (15% Tris-HCl ready gel made by Bio-Rad, Hercules, Calif.). After treatment with the fixing buffer (10% acetic acid, 10% methanol) and then Amplify (Amersham-Pharmacia, Piscataway, N.J.), the gels are dried and exposed to X-ray film or quantitatively analyzed utilizing phosphor image (Molecular Dynamics, Sunnyview, Calif.).

A Vif-Vif binding assay is performed similarly to the GST pull-down assays, except that the GST or GST-Vif conjugated bead slurry was mixed with $^{35}$S-labeled Vif and the test peptides or molecules in the binding buffer. The results are compared to that from the GST pull-down assay, which is designated as 100%.

Example 41

Demonstration that the Peptide of Amino Acid Sequence SEQ ID NO:1 Comprises a Minimum Sequence Necessary to Inhibit Viral Infectivity Various truncated analogues of the peptide of amino acid sequence SEQ ID NO:36 were prepared to determine the minimal peptide necessary to inhibit viral infectivity. The compounds were tested in a viral infectivity assay in which PBMCs were infected with HIV-1$_{NL4-3}$ viruses (MOI: 0.1). The amounts of virus produced were monitored by detecting the HIV-1 p24 antigen. level in the cell culture using p24 Gag ELISA (Zeptometrics). The results of these experiments are summarized in Table 4.

TABLE 4

Effect of Truncated Analogues of the Peptide of Amino Acid Sequence SEQ ID NO: 36 in Inhibiting HIV-1$_{NL4-3}$ Viruses in a Viral Infectivity Assay using Peripheral Blood Mononuclear Cells

| Analogue | Activity |
|---|---|
| Tyr Gly Arg Lys Lys Arg Arg Gln Arg Arg Arg Gly Gly Gly Ser Pro Leu Pro Arg Ser Val (SEQ ID NO: 74) | Inactive |
| Tyr Gly Arg Lys Lys Arg Arg Gln Arg Arg Arg Gly Ser Asn Gln Gly Gly Ser Pro Leu Pro Arg Ser (SEQ ID NO: 75) | Inactive |
| Tyr Gly Arg Lys Lys Arg Arg Gln Arg Arg Arg Gly Gln Gly Gly Ser Pro Leu Pro Arg Ser Val (SEQ ID NO: 2) | Active |

The peptide of amino acid sequence SEQ ID NO:2 has a M.W. of 2596 and a basic isoelectric point (pI) of 12.39 and a solubility of about 1 mg/mL.

Example 42

Demonstration that the Peptide of Amino Acid Sequence SEQ ID NO:2 Inhibits HIV-1$_{NL4-3}$ Viruses in Human T lymphoblastoid H9 Cell Line A viral infectivity assay was performed in the presence or absence of the peptides of amino acid sequence SEQ ID NO:2 and SEQ ID NO:36, and the control peptide of amino acid sequence SEQ ID NO:35 using HIV-1$_{NL4-3}$ viruses in H9 cells and assaying HIV-1 p24 antigen. The procedure was performed essentially as described by B. Yang, et al., *J. Bio. Chem.*, 2003; 278(8), 6596-602, which describes the method as follows. H9 cells (1×10$^6$) are mixed with HIV-1$_{NL4-3}$ viruses at a multiplicity of infection of 0.01. After incubation at 37° C. for 5 hours, the excess viruses were removed, and the cells are cultured in the presence of RPMI 1640 medium plus 100/% fetal bovine serum with or without the peptides at a concentration of 50 µM. Every 3-4 days the supernatants are harvested and refreshed. The effects of the peptides on viral infectivity are monitored by detecting the HIV-1 p24 antigen level in the cell culture supernatant via ELISA.

Figure 3:
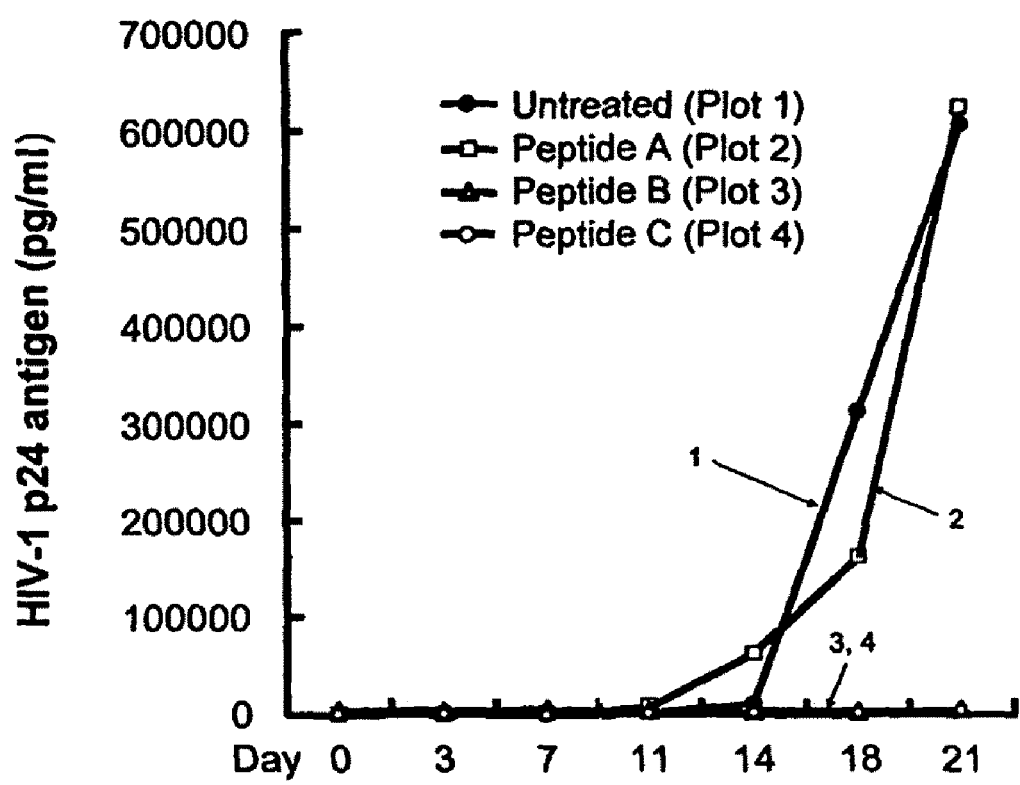
FIG. 3. Plot of HIV-1 p24.antigen levels (measured by ELISA) in the supernatants of cell cultures of in human T lymphoblastoid H9 cell line peptides infected HIV-1$_{NLA-3}$ viruses cultured in the presence of peptides of amino acid sequence SEQ ID NO:36 (Peptide A), SEQ ID NO:37 (Peptide B), or SEQ ID NO:2 (Peptide C) or untreated controls.
Figure 4A:
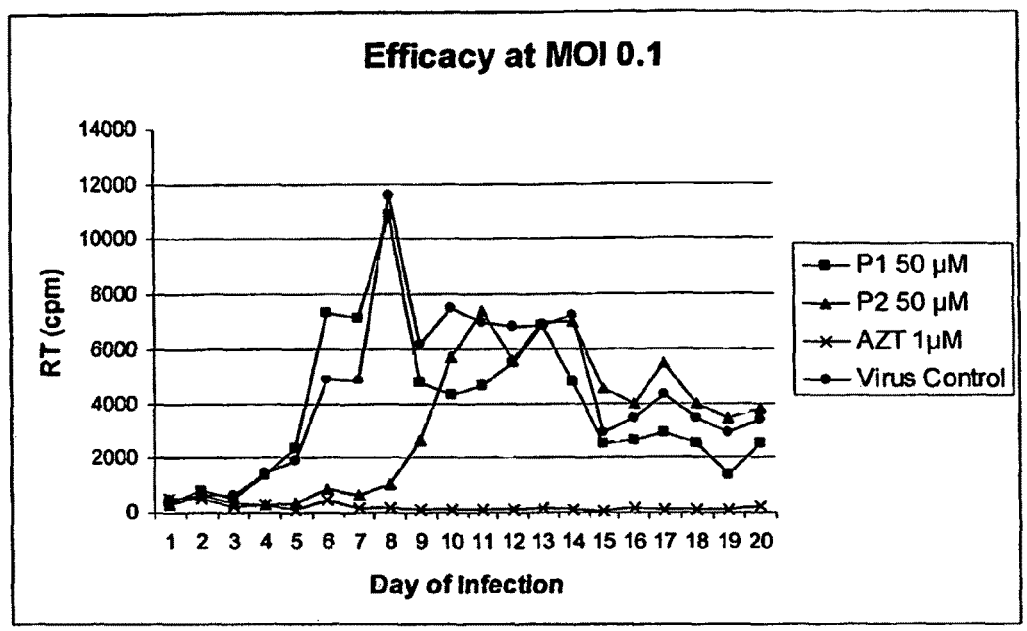
FIGS. 4A, 4B, 4C, and 4D. Antiviral activity of the peptide of amino acid sequence SEQ ID NO:36 at 50 μM in MT-2 cells with HIV-1$_{IIIB}$ virus at various multiplicities of infection (MOI). Virus production was assayed using a reverse transcriptase (RI) assay. Shown are plots of reverse transcriptase assays as a function of time for cultures of infected cells treated with peptide of amino acid sequence SEQ ID NO:36 at 50 μM ("P2 50 μM"), the peptide of amino acid sequence SEQ ID NO:35 at 50 μM ("P1 50 μm"), azidothymidine at 1 μM ("AZT 1 μM") and untreated controls ("virus control"). The results are shown for experiments conducted with infection of the cells carried out at multiplicities of infection of 0.1 (FIG. 4A), 0.03 (FIG. 4B), 0.01 (FIG. 4C), and 0.003 (FIG. 4D).
Figure 4B:
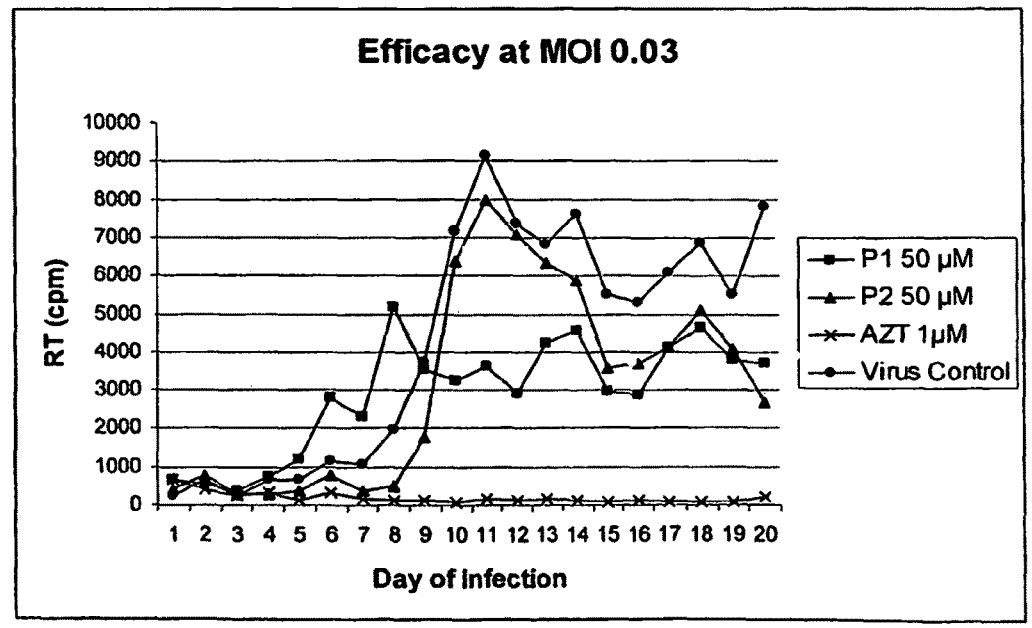
Figure 4C:
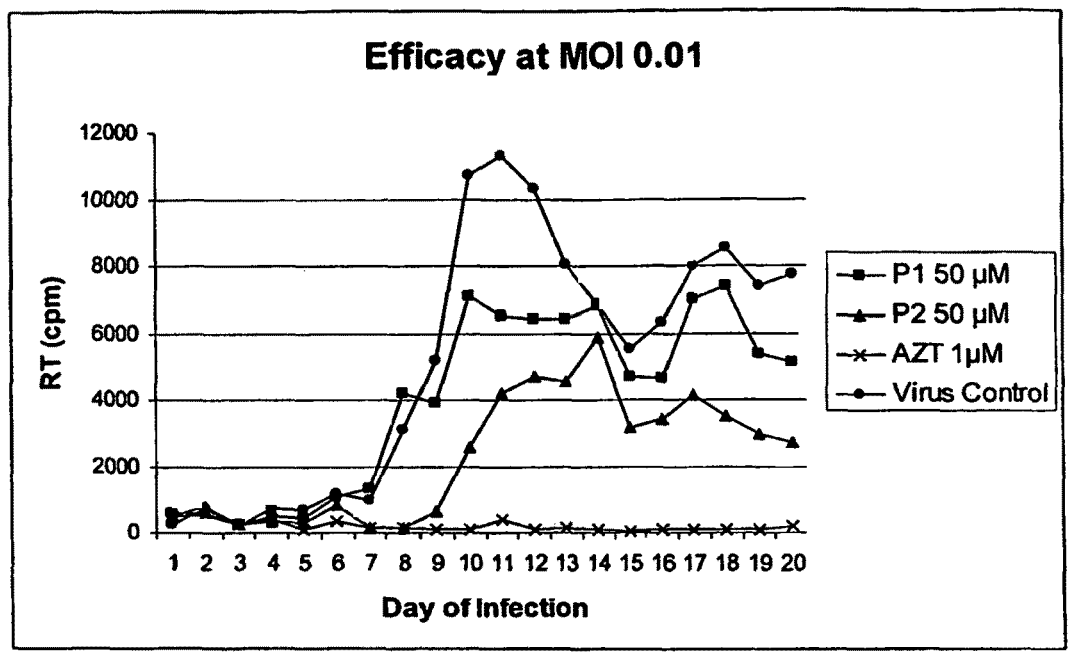
Figure 4D:
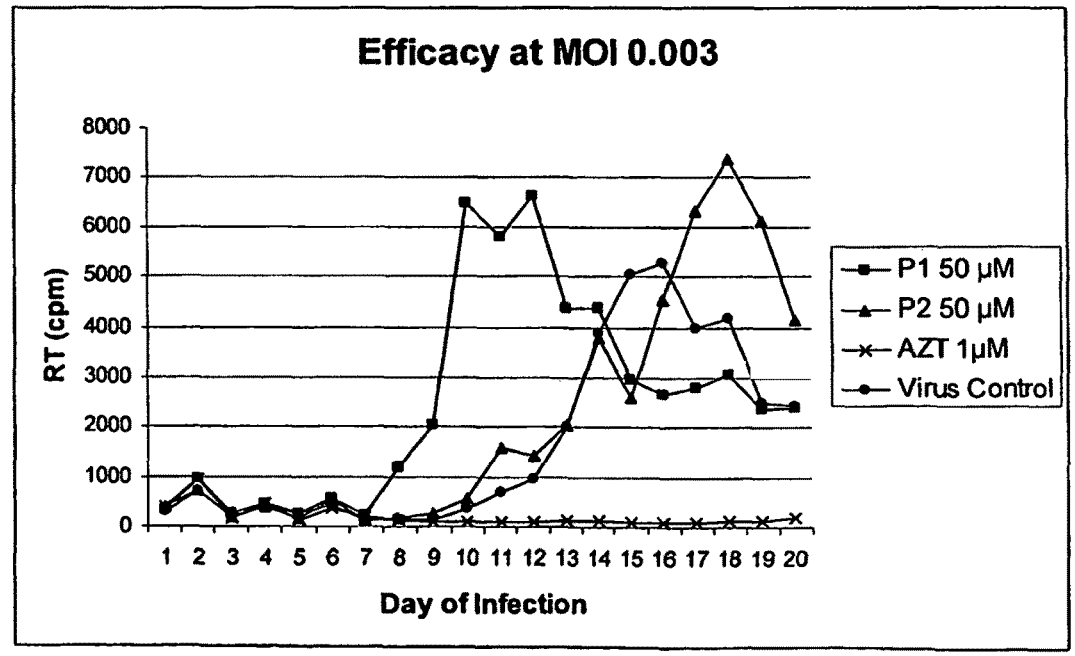
Figure 5A:
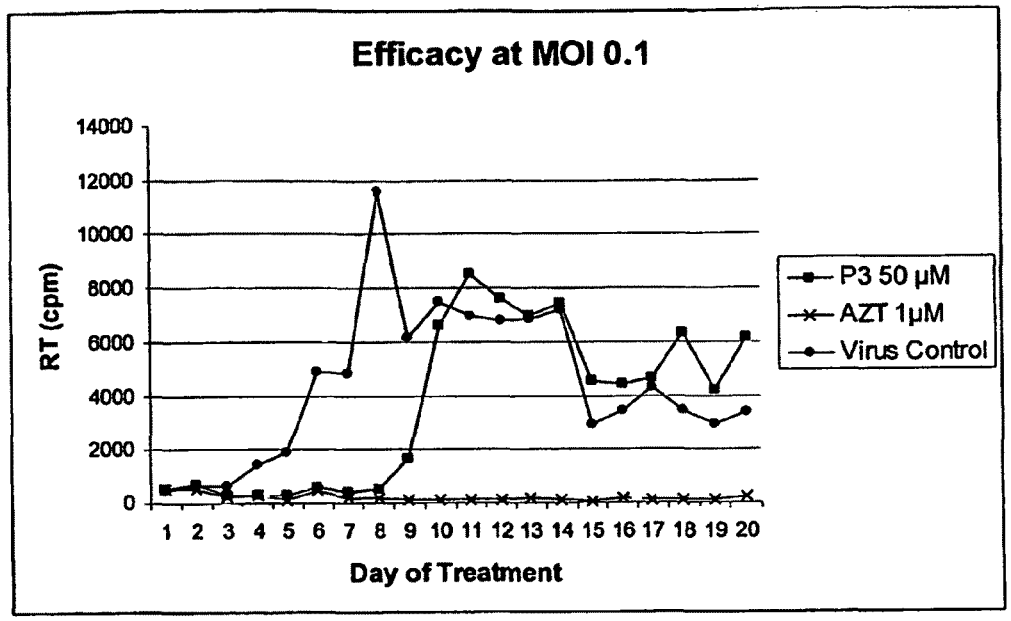
FIGS. 5A, 5B, 5C, and 5D. Antiviral activity of the peptide of amino acid sequence SEQ ID NO:2 at 50 μM in MT-2 cells with HIV-1$_{IIIB}$ virus at various multiplicities of infection (MOI). Virus production was assayed using a reverse transcriptase, (RT) assay. Shown are plots of reverse transcriptase assays as a function of time for cultures of infected cells treated with peptide of amino acid sequence SEQ ID NO:2 at 50 μM ("P3 50 μM"), the peptide of azidothymidine at 1 μM ("AZT 1 μM") and-untreated controls ("virus control"). The results are shown for experiments conducted with infection of the cells carried out at multiplicities of infection of 0.1 (FIG. 5A), 0.03 (FIG. 5B), 0.01 (FIG. 5C), and 0.003 (FIG. 5D).
Figure 5B:
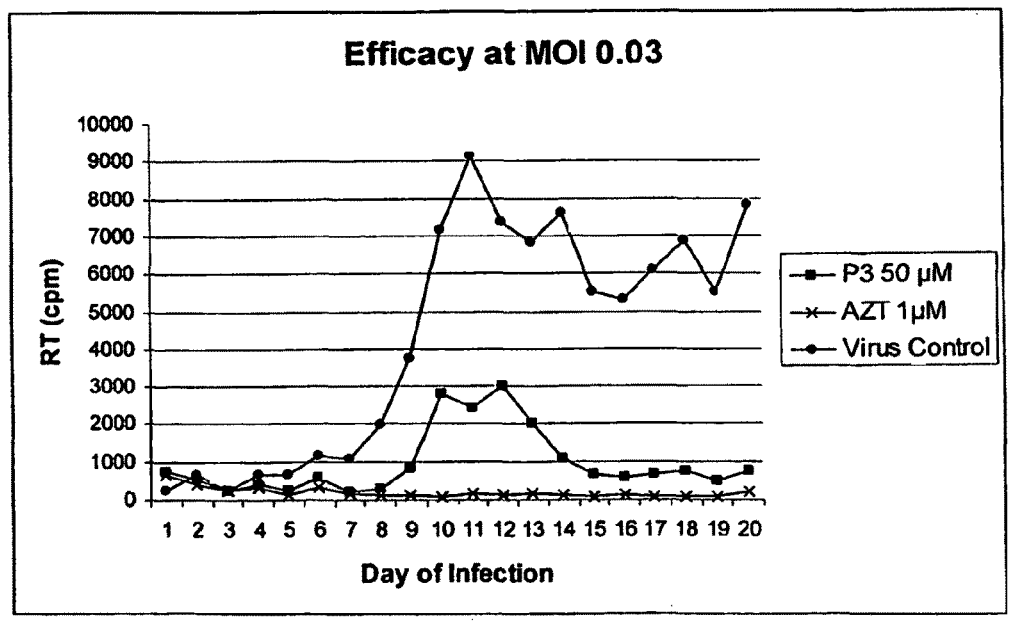
Figure 5C:
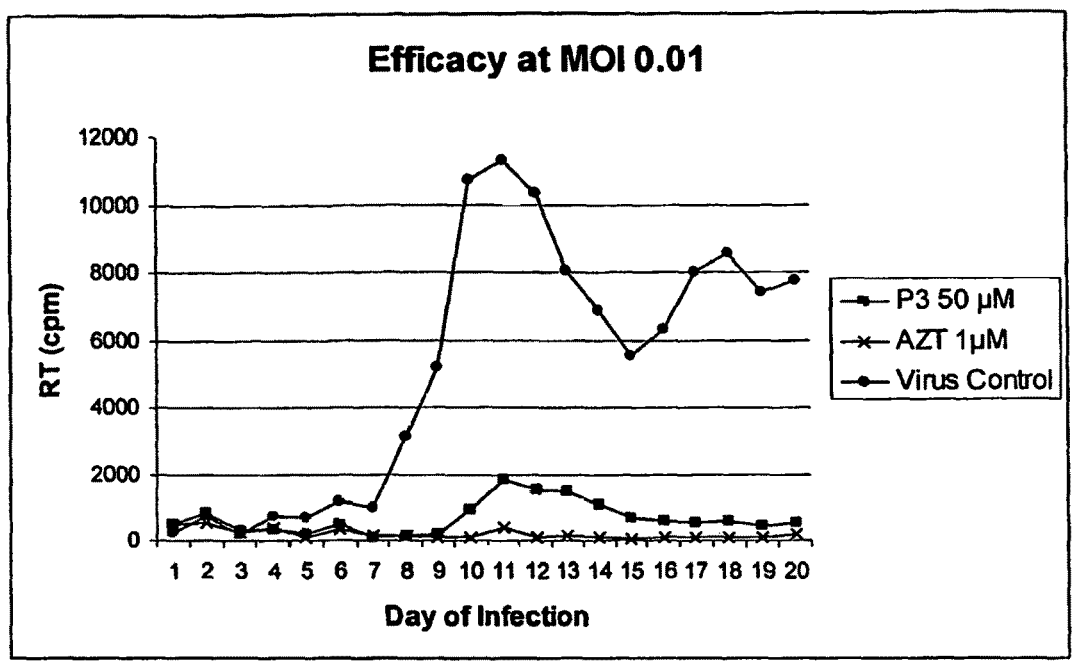
Figure 5D:
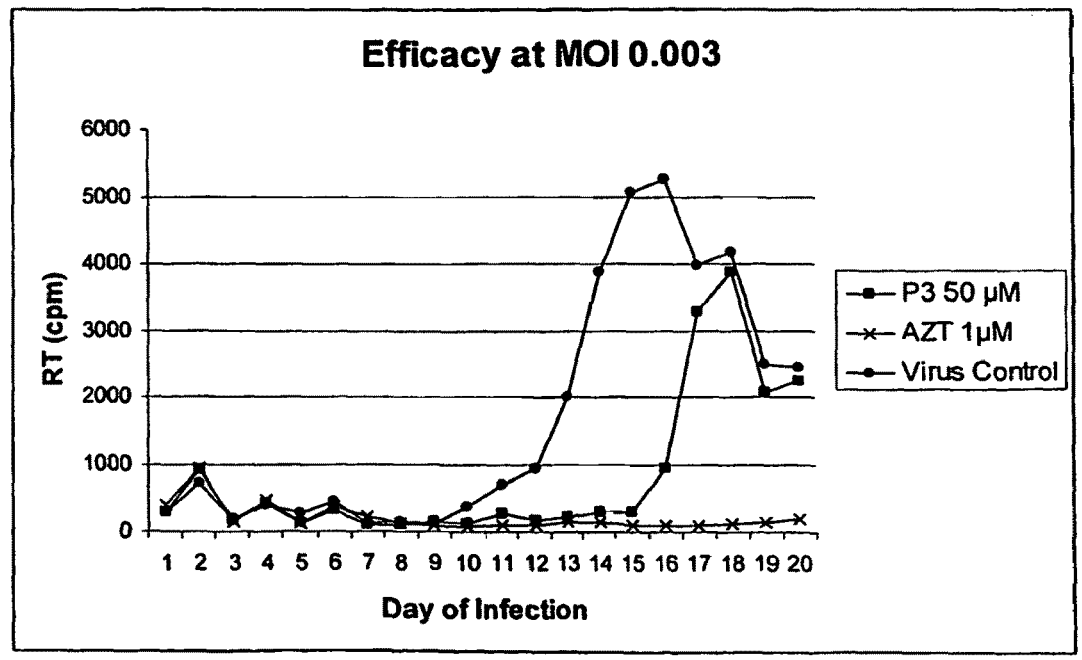

The results of these experiments are shown in FIG. 3. The peptides of amino acid sequence SEQ ID NO:2 and SEQ ID NO:36 both inhibited viral replication as compared to untreated cells, or cells treated with the control peptide of amino acid sequence SEQ ID NO:35.

Example 43

Procedure for the Evaluation of Compounds of the Invention in a Low Multiplicity of Infection Acute infection (MOI) Assay in MT-2 Cells MT-2 cells and a laboratory-adapted HIV-1$_{IIIB}$ strain were obtained from the AIDS Research and Reference Reagent Program, Rockville, Md.

The MT-2 cells were infected using the following standard protocol in 96-well microtiter plates. A solution of test compound or control (water as a negative control, or AZT as a positive control) (50 µL) at a known concentration were added in triplicate to MT-2 cells (50 µL) plated at a density of 2.5×10$^3$ cells per well. HIV-1$_{IIIB}$ virus was added to the wells in a volume of 100 µL at MOIs of 0.10, 0.032, 0.01, and 0.0032 µL/well). Virus replication in the infected MT-2 cells was monitored daily by a reverse transcriptase assay. The test compound (or control compound) was replenished every other day at the same known concentration in a volume corresponding to the volume of supernatant removed from to perform the reverse transcriptase assay. This was intended to maintain a reasonably constant concentration of compound in the well throughout the testing. Cultures were sub-cultured on days 8 and 14 by performing a 1:5 split of the culture to maintain the cells in a logarithmic growth mode. The sub-culturing involved the transfer of 20% of the volume of the well (cells and medium) into a well containing fresh tissue culture medium together with a fresh sample of the test compound (or control).

A reverse transcriptase activity assay to assess virus replication was performed using a radioactive incorporation polymerization assay, essentially as follows. Tritiated thymidine phosphate was purchased from Perkin Elmer at 1 Ci/mL and 1 µL was used per enzyme reaction. Poly rA and oligo dT were prepared at concentrations of 0.5 mg/mL and 1.7 Units/mL, respectively, from a stock solution which was kept at −20° C. The reverse transcriptase reaction buffer was prepared fresh on a daily basis and consists of 1M EGTA (125 µL), deionized water (125 µL), 20% Triton X-100 (125 µL), of Tris (pH 7.4) (50 µL), of DTT (50 µL), and MgCl$_2$ (1M, 40 µL). For each reaction tritiated thimidine phosphate (1 µL), of deionized water (4 µL), the poly rA and oligo dT solution (2.5 µL) and reaction buffer (2.5 µL) were mixed. The resulting reaction mixture (10 µL) was placed in a round bottom microtiter plate and virus-containing supernatant (15 µL) was added and mixed. The plate was incubated at 37° C. in a humidified incubator for 90 min, then 10 µL of the reaction volume was spotted onto DEAE filter mat in the appropriate plate format, washed 5 times for 5 minutes each in a 5% sodium phosphate buffer, 2 times for 1 minute each in distilled water, 2 times for 1 minute each in 70% ethanol and then air dried. The dried filter mat was placed in a plastic sleeve and OPTI-FLUOR® O (liquid scintillation cocktail, Perkin Elmer) was added to each sleeve. The incorporated radioactivity was measured with a liquid scintillation counter (Wallac 1450 MICROBETA® Trilux).

The above-described experiment was performed using the following peptides:

```
(1) Tyr Gly Arg Lys Lys Arg Arg Gln Arg Arg Arg Gly
    Asp Leu Gly Glu Gln His Phe Lys Gly Leu Val
    Leu.
    (SEQ ID NO: 35)

(2) Tyr Gly Arg Lys Lys Arg Arg Gln Arg Arg Arg Gly
    Ser Asn Gln Gly Gly Ser Pro Leu Pro Arg Ser
    Val.
    (SEQ ID NO: 36)

(2) Tyr Gly Arg Lys Lys Arg Arg Gln Arg Arg Arg Gly
    Gln Gly Gly Ser Pro Leu Pro Arg Ser Val.
    (SEQ ID NO: 2)
```

The results of the experiments are shown in FIGS. 4A-4D (comparing the peptides of amino acid sequence SEQ ID NO:35 and SEQ -ID NO:36 and FIG. 5A-5D (showing the results for the peptides of amino acid sequence SEQ ID NO:2). In addition to the data shown, a solvent control (mock treatment of the cells with water rather than a solution of test compound) and cell controls (MT-2 cells not infected with virus) were run side-by-side with the other experiments.

At high MOI (0.1) (FIGS. 4A and 5A) the control peptide (sequence SEQ ID NO:35) did not inhibit virus production, whereas the peptide of amino acid sequence SEQ ID NO:36 delayed the onset of virus production for approximately 4-5 days. The peptide of amino acid sequence SEQ ID NO:2 appeared to have approximately the same effect as the peptide of amino acid sequence SEQ ID NO:36, delaying the onset of virus production by about 5-6 days.

At medium-high MOI (0.03) (FIGS. 4B and 5B) similar effects were seen as at MOI 0.1 with the peptide of amino acid sequence SEQ ID NO:36 delaying the onset of virus production for approximately 2-3 days. The peptide of amino acid sequence SEQ ID NO:2 delayed the onset of virus production for approximately 3-4 days, but suppression was reestablished by day 15 after peaking at about day 11. The control peptide (sequence SEQ ID NO:35) did not inhibit virus production.

At medium-low MOI (0.01) (FIGS. 4C and 5C), the results were similar to those observed at MOI 0.03. The peptide of amino acid sequence. SEQ ID NO:36 delayed the onset of virus production for approximately 3-4 days, whereas the peptide of amino acid sequence SEQ ID NO:2 delayed the onset of virus production for approximately 5-6 days, and reestablished suppression by day 15-16 after peaking at about day 11. The control peptide (sequence SEQ ID NO:35) did not inhibit virus production.

At the lowest MOI tested (0.003) (FIGS. 4D and 4D), the peptide of amino acid sequence SEQ ID NO:36 did not appear to have any effect upon virus production: the results for the peptide appeared to track those for the virus control, and also the solvent control (data not shown). The control peptide (sequence SEQ ID NO:35) appeared to somewhat enhance virus production relative to the untreated cells. The peptide of amino acid sequence SEQ ID NO:2 afforded significant protection, delaying the onset of virus production for approximately 7-8 days compared to the virus control samples.

These results demonstrated that whereas the peptide of amino acid sequence SEQ ID NO:36 had activity in inhibiting virus production, the peptide of amino acid sequence SEQ ID NO:2 was markedly more effective at all but the highest MOIs tested, where the activity of the peptides of amino acid sequence SEQ ID NO:2 and SEQ ID NO:36 were comparable.

The results were also noteworthy in that a qualitative difference was observed between the curves for the peptide of amino acid sequence SEQ ID NO:2 as compared to the peptide of amino acid sequence SEQ ID NO:36, particularly at the MOIs of 0.03 and 0.01. As was described above, the peptide of amino acid sequence SEQ ID NO:36 was effective at delaying onset of virus replication, as judged by reverse transcriptase levels, but after the onset of virus replication, elevated reverse transcriptase levels were observed for the duration of the experiment. In contrast, the peptide of amino acid sequence SEQ ID NO:2 also showed an initial, delayed, rise in virus levels, but the virus levels subsequently peaked and suppression was re-established. This result suggests that the truncation of the Vif-binding sequence in compounds comprising the amino acid sequence SEQ ID NO:1, such as the peptide of amino acid sequence SEQ ID NO:2, results in compounds that are more effective at suppressing viral replication than compounds comprising the amino acid sequence SEQ ID NO:76, such as the peptide of the amino acid sequence SEQ ID NO:36. In particular, the results indicate that the compounds comprising the amino acid sequence SEQ ID NO:1, such as the peptide of amino acid sequence SEQ ID NO:2 will be particularly advantageous in being less susceptible to the development of viral resistance than compounds comprising the amino acid sequence SEQ ID NO:76 such as the peptide of the amino acid sequence SEQ ID NO:36.

Example 44

Demonstration that the Peptide of Amino Acid Sequence SEQ ID NO:2. Enters Cells

The peptide of amino acid sequence SEQ ID NO:2 was synthesized with a C-terminal fluoroscein isothiocyanate (FTIC) tag. The FITC tag enables fluorescence microscopy of living cells in order to evaluate cellular uptake and intracellular localization of the peptide. Cultures of H9 and MT-2 cells were grown in media as recommended by the American Tissue Culture Collection (ATCC) and each culture was treated once in culture with of the FTIC-tagged peptide of the amino acid sequence SEQ ID NO:2. The cells were then photographed in the culture dish with an inverted fluorescence microscopy at various time points. The images showed a rapid uptake of the FTIC-tagged peptide into cells such that fluorescence within cells was detected after 5 ninutes of the FTIC-tagged peptide treatment and intracellular localization of the FTIC-tagged peptide was apparent in all cells within 30 minutes. The intracellular distribution was both punctate and diffuse in the cytoplasm but little or no FTIC-tagged peptide was observed within the nuclei of cells. This distribution was sustained for 24-48 hours and diminished by over 50% by 72 hours post-treatment.

Figure 6:
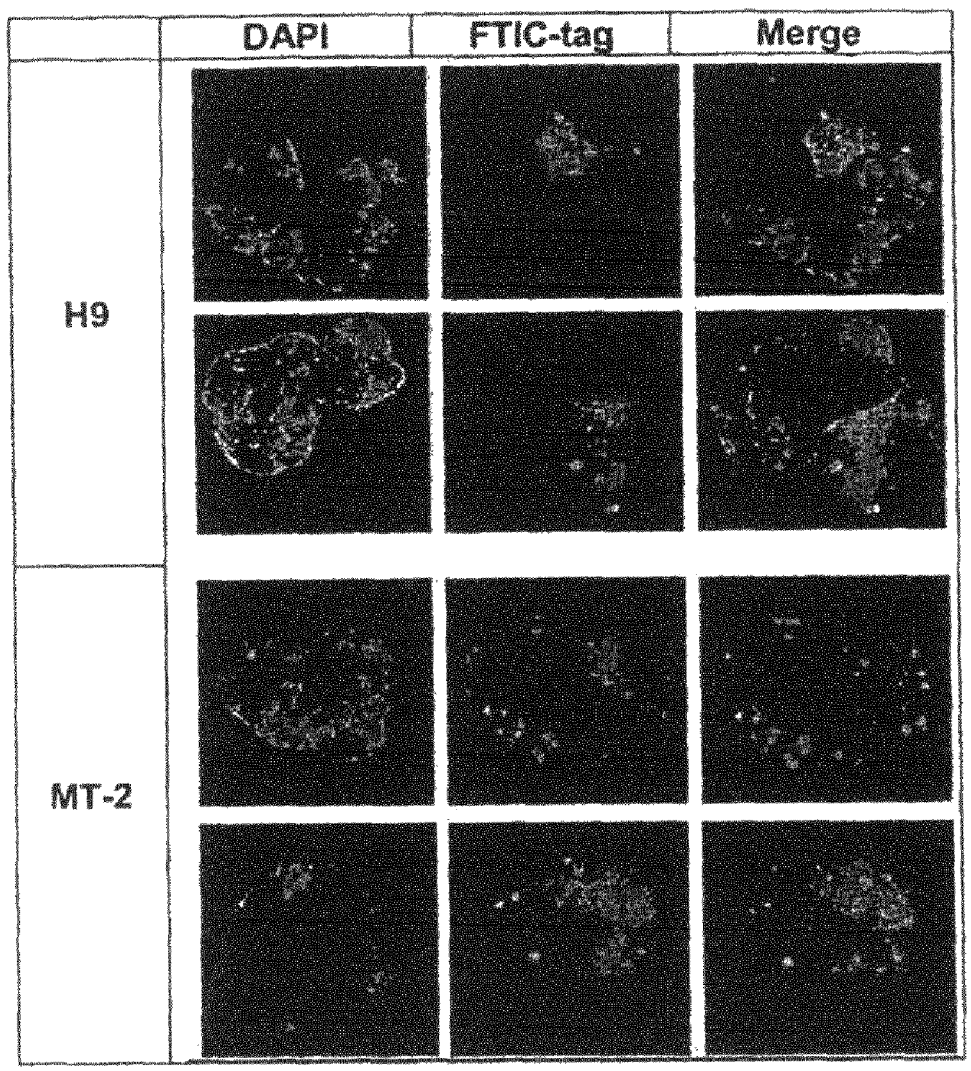
FIG. 6. Images obtained of H9 and MT-2 cells that were treated with the FTIC-tagged peptide of the amino acid sequence SEQ ID NO:2, then fixed with 2% paraformaldehyde, permeabilized with 0.4% Triton X-100 and stained with the DNA selective stain 4',6-diamidino-2-phenylindole (DAPI). Individual and image overlays (merge) of DAPI and FITC-tag staining for the cell nucleus and the tagged peptide of the amino acid sequence SEQ ID NO:2 respectively taken 24 h after a single treatment with 50 uM OYA-005-FITC. Two separate cells are shown for both H9 and MT-2 cells.

To highlight the position of the nucleus, H9 and MT-2 cells treated with the FTIC-tagged peptide of the amino acid sequence SEQ ID NO:2 as described above, fixed with 2% paraformaldehyde, permeabilized with 0.4% Triton X-100 and stained with the DNA selective stain 4',6-diamidino-2-phenylindole (DAPI). The results of this experiment are shown in FIG. 6. FIG. 6 shows individual and image overlays (merge) of DAPI and FITC-tag staining for the cell nucleus and the tagged peptide of the amino acid sequence SEQ ID NO:2 respectively taken 24 h after a single treatment with the FITC-tagged peptide. The results show that the FTIC-tagged peptide of the amino acid sequence SEQ ID NO:2 entered the cells, being localized in the cytoplasm but was not present in the nucleus.

Example 45

Demonstration that the Peptide of Amino Acid Sequence SEQ ID NO:2 Acts Specifically via the Postulated Vif/hAG3 Mechanism HEK 293T cells (that do not express hA3G) and HEK 293T cells transfected with hA3G cDNA were transfected with either proviral or Δvif virus DNA (lacking env) pseudotyped with VSV-G cDNA and allowed to produce viral particles. In this way, viruses both with and without Vif could be produced because the Δvif virus contains stop codons within the Vif coding sequence preventing Vif expression.

The cells were either left untreated or were treated with the peptide of the amino acid sequence SEQ ID NO:2 two hours prior to transfection, again 10 hours after transfection, and again 24 hours after transfection. Forty-eight hours after co-transfection, cell culture supernatants were harvested and filtered to obtain viral particles. The p24 (Gag) content of each virus stock was evaluated by ELISA (Zeptometrix) and the viral stocks were normalized to 10 ng of p24 before the next step, namely infection of JC53BL reporter cells in a 96-well plate.

The HeLa-CD4/CCR5 (C53) cell line expresses relatively high surface levels of both CD4 and CCR5 and is susceptible to infection by both R5 and X4 HIV-1 isolates. A reporter gene assay for infection by HIV-1 has been developed using JC53BL cells which express β-galactosidase and luciferase under the control of the HIV-1 promoter. X. Wei, et al., *Antimicrob. Agents Chemother.*, 2002, 46(6), 1896-1905.

The JC53BL reporter assay may therefore. be used to measure the infectivity of viruses produced by each of the cells. Infection was allowed to commence for 48 hours before cell lysis and the addition of Luciferase substrate (Promega). The produced luminescence was measured by a Victor 3 plate reader (Perkin Elmer). Luminescence levels correlated to the infectivity of virus produced under each condition.

Figure 7:
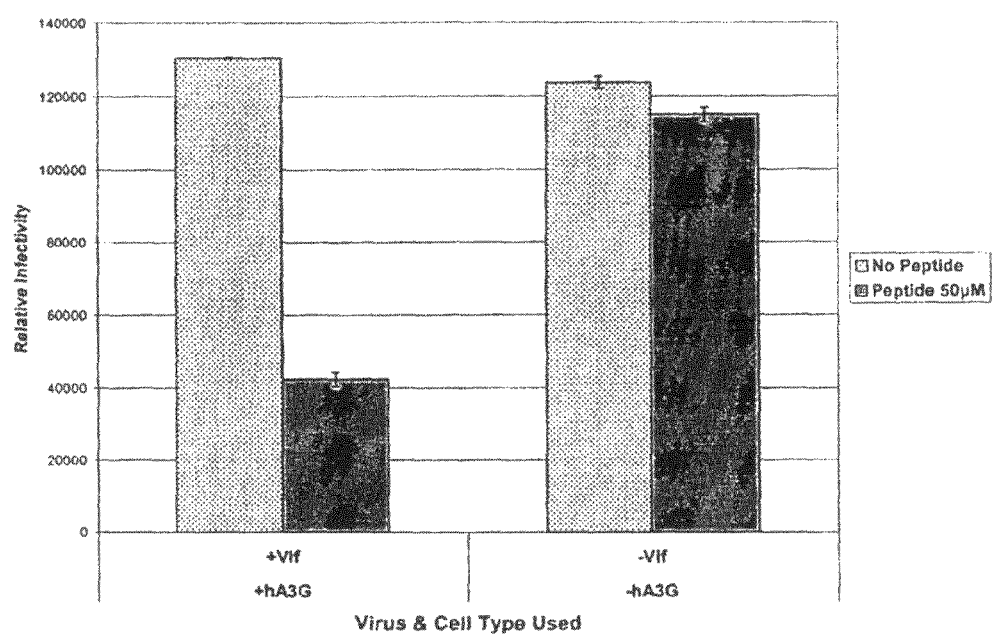
FIG. 7. Results of a JC53BL reporter cell infectivity assay with the cultures of viruses generated from human embryonic kidney (HEK) 293T cells transfected with hA3G gene and infected with VSV-G pseudotype HIV viruses ("+Vif, +hA3G") and HEK 293T (non-hA3G-expressing) cells infected with the Vif negative VSV-G pseudotype HIV viruses ("−Vif, −hA3G") either with treatment with the peptide of amino acid sequence SEQ ID NO:2 ("Peptide µM") or without such treatment ("No peptide").

FIG. 7 shows the results of the JC53BL reporter. cell infectivity assay with the cultures of viruses generated from HEK 293T cells transfected with hA3G gene and infected with the Vif positive viruses ("+Vif, +hA3G") and HEK 293T (non-hA3G-expressing) cells infected with the Vif negative viruses ("−Vif, −hA3G"). Without treatment with the peptide of amino acid sequence SEQ ID NO:2, the viruses generated from the HEK 293T cells transfected with hA3G gene and infected with the Vif positive viruses ("+Vif, +hA3G") produced infective viruses because the Vif-mediated destruction of hA3G overcomes the protective effect of hA3G. Likewise, the viruses viruses generated from the non-h3G-expressing HEK 293T cells infected with the Vif negative viruses ("−Vif; −hA3G") produce infective. viruses because the protective effect of hA3G is absent. Upon treatment with the peptide of amino acid sequence: SEQ ID NO:2, infectivity was reduced for the viruses produced by the hA3G expressing cells infected with Vif-positive viruses. No effect was observed on the infectivity of the viruses produced by the non-hA3G-expressing cells infected with Vif-negative viruses. This is consistent with the anti-viral effect of the peptide of amino acid sequence SEQ ID NO:2 being mediated by Vif inhibition, as inhibition of Vif restores the protective effect of hA3G. The hA3G hypermutates the viral DNA resulting in the production of fewer and/or defective (i.e. less infective) viruses. The reduced infectivity is not observed in the non-hA3G-expressing cells infected with Vif-negative viruses, suggesting that the peptide is not interfering with any process in the viral lifecycle not involving Vif and/or hA3G.

All references, including without limitation, all publications, patents, and published patent applications, cited herein within this specification are incorporated by reference. The present invention may be embodied in other specific forms without departing from the spirit or essential attributes thereof and, accordingly, reference should be made to the appended claims, rather than to the foregoing specification, as indication of the scope of the invention.

What is claimed is:

1. A compound according to the formula I:

$X^1$-M-SEQ ID NO:1    (I)

or a pharmaceutically acceptable salt thereof wherein:
   $X^1$-M- represents an optional group comprising, a protein transduction domain conjugated to the N-terminus of the amino acid sequence SEQ ID NO:1, wherein:
   $X^1$ represents the protein transduction domain;
   -M- represents a single bond or an optional linking group forming a covalent linkage between the protein transduction domain and the amino acid sequence SEQ ID NO:1; and
   the protein transduction domain comprises an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ NO:20, SEQ ID NO:21, SEQ ID NO:22, SEQ ID NO:23, SEQ ID NO:24, SEQ ID NO:25, SEQ ID NO:26, SEQ NO:27, SEQ ID NO:28, SEQ ID NO:29, SEQ ID NO:30, SEQ ID NO:31, SEQ ID NO:32, SEQ ID NO:33, and SEQ ID NO:34;
   provided that if the compound comprises an amino acid directly bound to the N-terminus of the amino acid sequence SEQ ID NO:1, then the amino acid directly bound to the N-terminus is other than asparagine.

2. The compound or pharmaceutically acceptable salt according to claim 1. wherein -M- consists of a single bond, an amino acid or a peptide.

3. The compound or pharmaceutically acceptable salt according to claim 2, wherein the compound of formula I comprises the amino acid sequence SEQ ID NO:3.

4. The compound or a pharmaceutically acceptable salt according to claim 1, wherein the protein transduction domain is directly linked at its C-terminus to -M-.

5. The compound or pharmaceutically acceptable salt according to claim 1 wherein the protein transduction domain comprises an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

6. The compound or pharmaceutically acceptable salt according to claim 5, wherein -M- consists of an amino acid or a peptide.

7. The compound or pharmaceutically acceptable salt according to claim 5, wherein -M- consists of a single bond.

8. The compound or pharmaceutically acceptable salt according to claim 5, wherein the protein transduction domain comprises the amino acid sequence SEQ ID NO:4.

9. The compound or pharmaceutically acceptable salt according to claim 7, wherein -M-consists of an amino acid or a peptide.

10. The compound or pharmaceutically acceptable salt according to claim 1, wherein the compound of formula I is a peptide consisting of an amino acid sequence selected from the group consisting of SEQ ID NO:1, SEQ ID NO:2, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ. ID NO:49, SEQ ID NO:50, SEQ ID NO:51, SEQ ID NO:52, SEQ NO:53, SEQ ID NO:54, SEQ ID NO:55, SEQ ID NO:56, SEQ ID NO:57, SEQ ID NO:58, SEQ ID NO:59, SEQ ID NO:60, SEQ NO:61, SEQ ID NO:62, SEQ ID NO:63, SEQ ID NO:64, SEQ ID NO:65, SEQ ID NO:66, SEQ ID NO:67, SEQ ID NO:68, SEQ NO:69, SEQ ID NO:70, SEQ ID NO:71, SEQ ID NO:72, and SEQ ID NO:73.

11. The compound or pharmaceutically acceptable salt according to claim 10, wherein the compound of formula I is a peptide consisting of the amino acid sequence SEQ ID NO: 1.

12. The compound or pharmaceutically acceptable salt according to claim 1, wherein the compound of formula I is a peptide consisting of the amino acid sequence SEQ ID NO:2.

13. A pharmaceutical composition comprising a pharmaceutically acceptable carrier and a compound or a pharmaceutically acceptable salt according to claim 1.

14. A method of treating a lentiviral disease in which Vif protein multimerization is required for viral replication in an individual, comprising administering to an individual in need of such treatment a therapeutically effective amount of a compound or a pharmaceutically acceptable salt according to claim 1.

15. A method of treating or reducing the risk of HIV-1 infection, comprising administering to an individual in need of such treatment or at risk of such infection a therapeutically effective amount of a compound or a pharmaceutically acceptable salt according to claim 1.

16. The method of claim 15, further comprising administering, in addition to the compound or pharmaceutically acceptable salt according to claim 1, at least one other therapeutic HIV-1 therapeutic compound.

17. The method of claim 16, wherein the at least one other HIV-1 therapeutic compound is selected, from the group consisting of protease inhibitors, reverse transcriptase inhibitors, and fusion inhibitors.

18. The method of claim 15 wherein the compound or pharmaceutically acceptable salt according to claim 1 is a peptide consisting of the amino acid sequence SEQ ID NO:2, or a pharmaceutically acceptable salt thereof.

19. A method of treating acquired immune deficiency syndrome, comprising administering to an individual in need of such treatment a therapeutically effective amount of a compound or a pharmaceutically acceptable salt according to claim 1.

20. The method of claim 19, further comprising administering, in addition to the compound or pharmaceutically acceptable salt according to claim 1, at least one other acquired immune deficiency syndrome therapeutic compound.

21. The method of claim 20, wherein the at least one other acquired immune deficiency syndrome therapeutic compound is selected from the group consisting of protease inhibitors, reverse transcriptase inhibitors, and fusion inhibitors.

22. The method of claim 19, wherein the compound or pharmaceutically acceptable salt according to claim 1 is a peptide consisting of the amino acid sequence SEQ ID NO:2 or a pharmaceutically acceptable salt thereof.

* * * * *

SEQUENCE LISTING

```
<160> NUMBER OF SEQ ID NOS: 76

<210> SEQ ID NO 1
<211> LENGTH: 10
<212> TYPE: PRT
<213> ORGANISM: Artificial Sequence
<220> FEATURE:
<223> OTHER INFORMATION: Vif-inhibitory peptide

<400> SEQUENCE: 1

Gln Gly Gly Ser Pro Leu Pro Arg Ser Val
1               5                   10

<210> SEQ ID NO 2
<211> LENGTH: 22
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 2

Tyr Gly Arg Lys Lys Arg Arg Gln Arg Arg Arg Gly Gln Gly Gly Ser
```

```
          1               5                  10                  15

Pro Leu Pro Arg Ser Val
                    20

<210> SEQ ID NO 3
<211> LENGTH: 11
<212> TYPE: PRT
<213> ORGANISM: Artificial Sequence
<220> FEATURE:
<223> OTHER INFORMATION: Vif-inhibitory peptide

<400> SEQUENCE: 3

Gly Gln Gly Gly Ser Pro Leu Pro Arg Ser Val
1               5                  10

<210> SEQ ID NO 4
<211> LENGTH: 12
<212> TYPE: PRT
<213> ORGANISM: human immunodeficiency virus

<400> SEQUENCE: 4

Tyr Gly Arg Lys Lys Arg Arg Gln Arg Arg Gly
1               5                  10

<210> SEQ ID NO 5
<211> LENGTH: 14
<212> TYPE: PRT
<213> ORGANISM: Human immunodeficiency virus

<400> SEQUENCE: 5

Gly Arg Lys Lys Arg Arg Gln Arg Arg Pro Pro Gln Cys
1               5                  10

<210> SEQ ID NO 6
<211> LENGTH: 13
<212> TYPE: PRT
<213> ORGANISM: human immunodeficiency virus

<400> SEQUENCE: 6

Gly Arg Lys Lys Arg Arg Gln Arg Arg Pro Pro Gln
1               5                  10

<210> SEQ ID NO 7
<211> LENGTH: 11
<212> TYPE: PRT
<213> ORGANISM: Human immunodeficiency virus

<400> SEQUENCE: 7

Tyr Gly Arg Lys Lys Arg Arg Gln Arg Arg
1               5                  10

<210> SEQ ID NO 8
<211> LENGTH: 11
<212> TYPE: PRT
<213> ORGANISM: Artificial Sequence
<220> FEATURE:
<223> OTHER INFORMATION: Synthetic sequence based on HIV TAT

<400> SEQUENCE: 8

Tyr Ala Arg Lys Ala Arg Arg Gln Ala Arg Arg
1               5                  10

<210> SEQ ID NO 9
<211> LENGTH: 11
<212> TYPE: PRT
<213> ORGANISM: Artificial Sequence
```

```
<220> FEATURE:
<223> OTHER INFORMATION: Synthetic sequence based on HIV TAT

<400> SEQUENCE: 9

Tyr Ala Arg Ala Ala Ala Arg Gln Ala Arg Ala
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic sequence based on HIV TAT

<400> SEQUENCE: 10

Tyr Ala Arg Ala Ala Arg Arg Ala Ala Arg Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic sequence based on HIV TAT

<400> SEQUENCE: 11

Tyr Ala Arg Ala Ala Arg Arg Ala Ala Arg Ala
1               5                   10

<210> SEQ ID NO 12
<211> LENGTH: 16
<212> TYPE: PRT
<213> ORGANISM: Drosophila melanogaster

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Reverse Sequence of pAntp (43-48)

<400> SEQUENCE: 13

Lys Lys Trp Lys Met Arg Arg Asn Gln Phe Trp Val Lys Val Gln Arg
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: W/R Penetratin

<400> SEQUENCE: 14

Arg Arg Trp Arg Arg Trp Trp Arg Arg Trp Trp Arg Arg Trp Arg Arg
1               5                   10                  15

<210> SEQ ID NO 15
<211> LENGTH: 7
<212> TYPE: PRT
<213> ORGANISM: Drosophila melanogaster

<400> SEQUENCE: 15

Arg Arg Met Lys Trp Lys Lys
```

<210> SEQ ID NO 16
<211> LENGTH: 7
<212> TYPE: PRT
<213> ORGANISM: Artificial Sequence
<220> FEATURE:
<223> OTHER INFORMATION: Chemically synthesized; Arginine 7-mer

<400> SEQUENCE: 16

Arg Arg Arg Arg Arg Arg Arg
1               5

<210> SEQ ID NO 17
<211> LENGTH: 9
<212> TYPE: PRT
<213> ORGANISM: Artificial Sequence
<220> FEATURE:
<223> OTHER INFORMATION: Chemically synthesized; Arginine 9-mer

<400> SEQUENCE: 17

Arg Arg Arg Arg Arg Arg Arg Arg Arg
1               5

<210> SEQ ID NO 18
<211> LENGTH: 30
<212> TYPE: PRT
<213> ORGANISM: Herpes simplex virus 1

<400> SEQUENCE: 18

Asp Ala Ala Thr Arg Ser Ala Ala Ser Arg Pro Thr Glu Arg Pro Arg
1               5                   10                  15

Ala Pro Ala Arg Ser Ala Ser Arg Pro Arg Arg Pro Val Glu
            20                  25                  30

<210> SEQ ID NO 19
<211> LENGTH: 16
<212> TYPE: PRT
<213> ORGANISM: Human immunodeficiency virus

<400> SEQUENCE: 19

Gly Ala Leu Phe Leu Gly Trp Leu Gly Ala Ala Gly Ser Thr Met Gly
1               5                   10                  15

<210> SEQ ID NO 20
<211> LENGTH: 27
<212> TYPE: PRT
<213> ORGANISM: Human immunodeficiency virus

<400> SEQUENCE: 20

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 21
<211> LENGTH: 27
<212> TYPE: PRT
<213> ORGANISM: Artificial Sequence
<220> FEATURE:
<223> OTHER INFORMATION: Caiman crocodylus Ig(v) light chain- SN40NLS

<400> SEQUENCE: 21

Met Gly Leu Gly Leu His Leu Leu Val Leu Ala Ala Ala Leu Gln Gly
1               5                   10                  15

```
Ala Trp Ser Gln Pro Lys Lys Arg Lys Val
            20                  25

<210> SEQ ID NO 22
<211> LENGTH: 12
<212> TYPE: PRT
<213> ORGANISM: Hepatitis B virus

<400> SEQUENCE: 22

Pro Leu Ser Ser Ile Phe Ser Arg Ile Gly Asp Pro
1               5                   10

<210> SEQ ID NO 23
<211> LENGTH: 12
<212> TYPE: PRT
<213> ORGANISM: Hepatitis B virus

<400> SEQUENCE: 23

Phe Trp Arg Gly Asp Leu Val Phe Asp Phe Gln Val
1               5                   10

<210> SEQ ID NO 24
<211> LENGTH: 25
<212> TYPE: PRT
<213> ORGANISM: Vesicular stomatitis virus

<400> SEQUENCE: 24

Lys Phe Thr Ile Val Phe Pro His Asn Gln Lys Gly Asn Trp Lys Asn
1               5                   10                  15

Val Pro Ser Asn Tyr His Tyr Cys Pro
            20                  25

<210> SEQ ID NO 25
<211> LENGTH: 20
<212> TYPE: PRT
<213> ORGANISM: Artificial Sequence
<220> FEATURE:
<223> OTHER INFORMATION: Chemically synthesized; fragment of human
      adenovirus fiber protein

<400> SEQUENCE: 25

Ala Lys Arg Ala Arg Leu Ser Thr Ser Phe Asn Pro Val Tyr Pro Tyr
1               5                   10                  15

Glu Asp Glu Ser
            20

<210> SEQ ID NO 26
<211> LENGTH: 27
<212> TYPE: PRT
<213> ORGANISM: Artificial Sequence
<220> FEATURE:
<223> OTHER INFORMATION: Transportan

<400> SEQUENCE: 26

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 27
<211> LENGTH: 18
<212> TYPE: PRT
<213> ORGANISM: Artificial Sequence
<220> FEATURE:
<223> OTHER INFORMATION: synthetic peptide called SynB1
```

```
<400> SEQUENCE: 27

Arg Gly Gly Arg Leu Ser Tyr Ser Arg Arg Phe Ser Thr Ser Thr
1               5                   10                  15

Gly Arg

<210> SEQ ID NO 28
<211> LENGTH: 16
<212> TYPE: PRT
<213> ORGANISM: Karposi's sarcoma-associated herpesvirus

<400> SEQUENCE: 28

Ala Ala Val Ala Leu Leu Pro Ala Val Leu Leu Ala Leu Leu Ala Pro
1               5                   10                  15

<210> SEQ ID NO 29
<211> LENGTH: 12
<212> TYPE: PRT
<213> ORGANISM: Karposi's sarcoma-associated herpesvirus

<400> SEQUENCE: 29

Ala Ala Val Leu Leu Pro Val Leu Leu Ala Ala Pro
1               5                   10

<210> SEQ ID NO 30
<211> LENGTH: 15
<212> TYPE: PRT
<213> ORGANISM: Homo sapiens

<400> SEQUENCE: 30

Val Thr Val Leu Ala Leu Gly Ala Leu Ala Gly Val Gly Val Gly
1               5                   10                  15

<210> SEQ ID NO 31
<211> LENGTH: 30
<212> TYPE: PRT
<213> ORGANISM: Artificial Sequence
<220> FEATURE:
<223> OTHER INFORMATION: P3 Membrane Fusion Sequence

<400> SEQUENCE: 31

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 32
<211> LENGTH: 18
<212> TYPE: PRT
<213> ORGANISM: Artificial Sequence
<220> FEATURE:
<223> OTHER INFORMATION: Model ambiphilic peptide

<400> SEQUENCE: 32

Lys Leu Ala Leu Lys Leu Ala Leu Lys Ala Leu Lys Ala Ala Leu Lys
1               5                   10                  15

Leu Ala

<210> SEQ ID NO 33
<211> LENGTH: 30
<212> TYPE: PRT
<213> ORGANISM: Artificial Sequence
<220> FEATURE:
<223> OTHER INFORMATION: Model ambiphilic peptide

<400> SEQUENCE: 33
```

```
Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 34
<211> LENGTH: 12
<212> TYPE: PRT
<213> ORGANISM: Artificial Sequence
<220> FEATURE:
<223> OTHER INFORMATION: Synthetic protein transduction domain

<400> SEQUENCE: 34

Arg Arg Gln Arg Arg Thr Ser Lys Leu Met Lys Arg
1               5                   10

<210> SEQ ID NO 35
<211> LENGTH: 24
<212> TYPE: PRT
<213> ORGANISM: Artificial Sequence
<220> FEATURE:
<223> OTHER INFORMATION: control sequence linked to protein transduction
      domain

<400> SEQUENCE: 35

Tyr Gly Arg Lys Lys Arg Arg Gln Arg Arg Gly Asp Leu Gly Glu
1               5                   10                  15

Gln His Phe Lys Gly Leu Val Leu
            20

<210> SEQ ID NO 36
<211> LENGTH: 24
<212> TYPE: PRT
<213> ORGANISM: Artificial Sequence
<220> FEATURE:
<223> OTHER INFORMATION: Vif-inhibitory peptide linked to protein
      transduction domain

<400> SEQUENCE: 36

Tyr Gly Arg Lys Lys Arg Arg Gln Arg Arg Gly Ser Asn Gln Gly
1               5                   10                  15

Gly Ser Pro Leu Pro Arg Ser Val
            20

<210> SEQ ID NO 37
<211> LENGTH: 24
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 37

Gly Arg Lys Lys Arg Arg Gln Arg Arg Pro Pro Gln Cys Gln Gly
1               5                   10                  15

Gly Ser Pro Leu Pro Arg Ser Val
            20

<210> SEQ ID NO 38
<211> LENGTH: 23
<212> TYPE: PRT
<213> ORGANISM: Artificial Sequence
<220> FEATURE:
<223> OTHER INFORMATION: Protein transduction domain-linked Vif-
      inhibitory peptide
```

-continued

```
<400> SEQUENCE: 38

Gly Arg Lys Lys Arg Arg Gln Arg Arg Pro Pro Gln Gln Gly Gly
1               5                   10                  15
Ser Pro Leu Pro Arg Ser Val
            20

<210> SEQ ID NO 39
<211> LENGTH: 21
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 39

Tyr Gly Arg Lys Lys Arg Arg Gln Arg Arg Gln Gly Gly Ser Pro
1               5                   10                  15
Leu Pro Arg Ser Val
            20

<210> SEQ ID NO 40
<211> LENGTH: 21
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 40

Tyr Ala Arg Lys Ala Arg Arg Gln Ala Arg Arg Gln Gly Gly Ser Pro
1               5                   10                  15
Leu Pro Arg Ser Val
            20

<210> SEQ ID NO 41
<211> LENGTH: 21
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 41

Tyr Ala Arg Ala Ala Ala Arg Gln Ala Arg Ala Gln Gly Gly Ser Pro
1               5                   10                  15
Leu Pro Arg Ser Val
            20

<210> SEQ ID NO 42
<211> LENGTH: 21
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 42

Tyr Ala Arg Ala Ala Arg Arg Ala Ala Arg Arg Gln Gly Gly Ser Pro
1               5                   10                  15
Leu Pro Arg Ser Val
            20

<210> SEQ ID NO 43
<211> LENGTH: 21
<212> TYPE: PRT
```

```
<213> ORGANISM: Artificial Sequence
<220> FEATURE:
<223> OTHER INFORMATION: Protein transduction domain-linked Vif-
      inhibitory peptide

<400> SEQUENCE: 43

Tyr Ala Arg Ala Ala Arg Arg Ala Ala Arg Ala Gln Gly Gly Ser Pro
 1               5                  10                  15

Leu Pro Arg Ser Val
            20

<210> SEQ ID NO 44
<211> LENGTH: 25
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 44

Gly Arg Lys Lys Arg Arg Gln Arg Arg Arg Pro Pro Gly Gln Cys Gln
 1               5                  10                  15

Gly Gly Ser Pro Leu Pro Arg Ser Val
            20                  25

<210> SEQ ID NO 45
<211> LENGTH: 24
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 45

Gly Arg Lys Lys Arg Arg Gln Arg Arg Arg Pro Pro Gly Gln Gln Gly
 1               5                  10                  15

Gly Ser Pro Leu Pro Arg Ser Val
            20

<210> SEQ ID NO 46
<211> LENGTH: 22
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 46

Tyr Gly Arg Lys Lys Arg Arg Gln Arg Arg Arg Gly Gln Gly Gly Ser
 1               5                  10                  15

Pro Leu Pro Arg Ser Val
            20

<210> SEQ ID NO 47
<211> LENGTH: 22
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 47

Tyr Ala Arg Lys Ala Arg Arg Gln Ala Arg Arg Gly Gln Gly Gly Ser
 1               5                  10                  15

Pro Leu Pro Arg Ser Val
            20
```

<210> SEQ ID NO 48
<211> LENGTH: 22
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 48

Tyr Ala Arg Ala Ala Ala Arg Gln Ala Arg Ala Gly Gln Gly Gly Ser
1               5                   10                  15

Pro Leu Pro Arg Ser Val
            20

<210> SEQ ID NO 49
<211> LENGTH: 22
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 49

Tyr Ala Arg Ala Ala Arg Arg Ala Ala Arg Arg Gly Gln Gly Gly Ser
1               5                   10                  15

Pro Leu Pro Arg Ser Val
            20

<210> SEQ ID NO 50
<211> LENGTH: 22
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 50

Tyr Ala Arg Ala Ala Arg Arg Ala Ala Arg Ala Gly Gln Gly Gly Ser
1               5                   10                  15

Pro Leu Pro Arg Ser Val
            20

<210> SEQ ID NO 51
<211> LENGTH: 26
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 51

Arg Gln Ile Lys Ile Trp Phe Gln Asn Arg Arg Met Lys Trp Lys Lys
1               5                   10                  15

Gln Gly Gly Ser Pro Leu Pro Arg Ser Val
            20                  25

<210> SEQ ID NO 52
<211> LENGTH: 26
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 52

Lys Lys Trp Lys Met Arg Arg Asn Gln Phe Trp Val Lys Val Gln Arg
1               5                   10                  15

Gln Gly Gly Ser Pro Leu Pro Arg Ser Val
            20                  25

<210> SEQ ID NO 53
<211> LENGTH: 26
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 53

Arg Arg Trp Arg Arg Trp Trp Arg Arg Trp Trp Arg Arg Trp Arg Arg
1               5                   10                  15

Gln Gly Gly Ser Pro Leu Pro Arg Ser Val
            20                  25

<210> SEQ ID NO 54
<211> LENGTH: 17
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 54

Arg Arg Met Lys Trp Lys Lys Gln Gly Gly Ser Pro Leu Pro Arg Ser
1               5                   10                  15

Val

<210> SEQ ID NO 55
<211> LENGTH: 17
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 55

Arg Arg Arg Arg Arg Arg Arg Gln Gly Gly Ser Pro Leu Pro Arg Ser
1               5                   10                  15

Val

<210> SEQ ID NO 56
<211> LENGTH: 19
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 56

Arg Arg Arg Arg Arg Arg Arg Arg Arg Gln Gly Gly Ser Pro Leu Pro
1               5                   10                  15

Arg Ser Val

<210> SEQ ID NO 57
<211> LENGTH: 40
<212> TYPE: PRT
<213> ORGANISM: Artificial Sequence
<220> FEATURE:
<223> OTHER INFORMATION: Protein transduction domain-linked Vif-
      inhibitory peptide -continued

```
<400> SEQUENCE: 57

Asp Ala Ala Thr Arg Ser Ala Ser Arg Pro Thr Glu Arg Pro Arg
 1               5                  10                  15

Ala Pro Ala Arg Ser Ala Ser Arg Pro Arg Arg Pro Val Glu Gln Gly
                20                  25                  30

Gly Ser Pro Leu Pro Arg Ser Val
            35                  40

<210> SEQ ID NO 58
<211> LENGTH: 26
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 58

Gly Ala Leu Phe Leu Gly Trp Leu Gly Ala Ala Gly Ser Thr Met Gly
 1               5                  10                  15

Gln Gly Gly Ser Pro Leu Pro Arg Ser Val
                20                  25

<210> SEQ ID NO 59
<211> LENGTH: 37
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 59

Gly Ala Leu Phe Leu Gly Phe Leu Gly Ala Ala Gly Ser Thr Met Gly
 1               5                  10                  15

Ala Trp Ser Gln Pro Lys Ser Lys Arg Lys Val Gln Gly Gly Ser Pro
                20                  25                  30

Leu Pro Arg Ser Val
        35

<210> SEQ ID NO 60
<211> LENGTH: 37
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 60

Met Gly Leu Gly Leu His Leu Leu Val Leu Ala Ala Ala Leu Gln Gly
 1               5                  10                  15

Ala Trp Ser Gln Pro Lys Lys Lys Arg Lys Val Gln Gly Gly Ser Pro
                20                  25                  30

Leu Pro Arg Ser Val
        35

<210> SEQ ID NO 61
<211> LENGTH: 22
<212> TYPE: PRT
<213> ORGANISM: Artificial Sequence
<220> FEATURE:
<223> OTHER INFORMATION: Protein transduction domain-linked Vif-
      inhibitory peptide
```

-continued

```
<400> SEQUENCE: 61

Pro Leu Ser Ser Ile Phe Ser Arg Ile Gly Asp Pro Gln Gly Gly Ser
1               5                   10                  15

Pro Leu Pro Arg Ser Val
            20

<210> SEQ ID NO 62
<211> LENGTH: 22
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 62

Phe Trp Arg Gly Asp Leu Val Phe Asp Phe Gln Val Gln Gly Gly Ser
1               5                   10                  15

Pro Leu Pro Arg Ser Val
            20

<210> SEQ ID NO 63
<211> LENGTH: 35
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 63

Lys Phe Thr Ile Val Phe Pro His Asn Gln Lys Gly Asn Trp Lys Asn
1               5                   10                  15

Val Pro Ser Asn Tyr His Tyr Cys Pro Gln Gly Gly Ser Pro Leu Pro
            20                  25                  30

Arg Ser Val
        35

<210> SEQ ID NO 64
<211> LENGTH: 30
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 64

Ala Lys Arg Ala Arg Leu Ser Thr Ser Phe Asn Pro Val Tyr Pro Tyr
1               5                   10                  15

Glu Asp Glu Ser Gln Gly Gly Ser Pro Leu Pro Arg Ser Val
            20                  25                  30

<210> SEQ ID NO 65
<211> LENGTH: 37
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 65

Gly Trp Thr Leu Asn Ser Ala Gly Tyr Leu Leu Gly Lys Ile Asn Leu
1               5                   10                  15
```

Lys Ala Leu Ala Ala Leu Ala Lys Lys Ile Leu Gln Gly Gly Ser Pro
            20                  25                  30

Leu Pro Arg Ser Val
        35

<210> SEQ ID NO 66
<211> LENGTH: 28
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 66

Arg Gly Gly Arg Leu Ser Tyr Ser Arg Arg Arg Phe Ser Thr Ser Thr
1               5                   10                  15

Gly Arg Gln Gly Gly Ser Pro Leu Pro Arg Ser Val
            20                  25

<210> SEQ ID NO 67
<211> LENGTH: 26
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 67

Ala Ala Val Ala Leu Leu Pro Ala Val Leu Leu Ala Leu Leu Ala Pro
1               5                   10                  15

Gln Gly Gly Ser Pro Leu Pro Arg Ser Val
            20                  25

<210> SEQ ID NO 68
<211> LENGTH: 22
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 68

Ala Ala Val Leu Leu Pro Val Leu Leu Ala Ala Pro Gln Gly Gly Ser
1               5                   10                  15

Pro Leu Pro Arg Ser Val
            20

<210> SEQ ID NO 69
<211> LENGTH: 25
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 69

Val Thr Val Leu Ala Leu Gly Ala Leu Ala Gly Val Gly Val Gly Gln
1               5                   10                  15

Gly Gly Ser Pro Leu Pro Arg Ser Val
            20                  25

<210> SEQ ID NO 70
<211> LENGTH: 40
<212> TYPE: PRT
<213> ORGANISM: Artificial Sequence

```
<220> FEATURE:
<223> OTHER INFORMATION: Protein transduction domain-linked Vif-
      inhibitory peptide

<400> SEQUENCE: 70

Val Ala Tyr Ile Ser Arg Gly Gly Val Ser Thr Tyr Tyr Ser Asp Thr
 1               5                  10                  15

Val Lys Gly Arg Phe Thr Arg Gln Lys Tyr Asn Lys Arg Ala Gln Gly
                20                  25                  30

Gly Ser Pro Leu Pro Arg Ser Val
            35                  40

<210> SEQ ID NO 71
<211> LENGTH: 28
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 71

Lys Leu Ala Leu Lys Leu Ala Leu Lys Ala Leu Lys Ala Ala Leu Lys
 1               5                  10                  15

Leu Ala Gln Gly Gly Ser Pro Leu Pro Arg Ser Val
                20                  25

<210> SEQ ID NO 72
<211> LENGTH: 40
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 72

Trp Glu Ala Lys Leu Ala Lys Ala Leu Ala Lys Ala Leu Ala Lys His
 1               5                  10                  15

Leu Ala Lys Ala Leu Ala Lys Ala Leu Lys Ala Cys Glu Ala Gln Gly
                20                  25                  30

Gly Ser Pro Leu Pro Arg Ser Val
            35                  40

<210> SEQ ID NO 73
<211> LENGTH: 22
<212> TYPE: PRT
<213> ORGANISM: Artificial sequence
<220> FEATURE:
<223> OTHER INFORMATION: Protein transduction domain-linked Vif-
      inhibitory peptide

<400> SEQUENCE: 73

Arg Arg Gln Arg Arg Thr Ser Lys Leu Met Lys Arg Gln Gly Gly Ser
 1               5                  10                  15

Pro Leu Pro Arg Ser Val
            20

<210> SEQ ID NO 74
<211> LENGTH: 21
<212> TYPE: PRT
<213> ORGANISM: Artificial Sequence
<220> FEATURE:
<223> OTHER INFORMATION: Protein transduction domain-linked Vif-
      inhibitory peptide
```

```
<400> SEQUENCE: 74

Tyr Gly Arg Lys Lys Arg Arg Gln Arg Arg Arg Gly Gly Gly Ser Pro
1               5                   10                  15

Leu Pro Arg Ser Val
            20

<210> SEQ ID NO 75
<211> LENGTH: 23
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 75

Tyr Gly Arg Lys Lys Arg Arg Gln Arg Arg Arg Gly Ser Asn Gln Gly
1               5                   10                  15

Gly Ser Pro Leu Pro Arg Ser
            20

<210> SEQ ID NO 76
<211> LENGTH: 12
<212> TYPE: PRT
<213> ORGANISM: Artificial Sequence
<220> FEATURE:
<223> OTHER INFORMATION: Protein transduction domain-linked Vif-
      inhibitory peptide

<400> SEQUENCE: 76

Ser Asn Gln Gly Gly Ser Pro Leu Pro Arg Ser Val
1               5                   10
```